(12) United States Patent
Rob et al.

(10) Patent No.: US 7,610,115 B2
(45) Date of Patent: Oct. 27, 2009

(54) AUTOMATED PHARMACY ADMIXTURE SYSTEM (APAS)

(75) Inventors: Ronald H. Rob, Dugald (CA); Walter W. Eliuk, Winnipeg (CA); Lance R. Mlodzinski, Winnipeg (CA)

(73) Assignee: Intelligent Hospital Systems Ltd., Winnipeg (CA)

( * ) Notice: Subject to any disclaimer, the term of this patent is extended or adjusted under 35 U.S.C. 154(b) by 633 days.

(21) Appl. No.: 11/316,795

(22) Filed: Dec. 22, 2005

(65) Prior Publication Data

US 2006/0136095 A1    Jun. 22, 2006

Related U.S. Application Data

(60) Provisional application No. 60/638,776, filed on Dec. 22, 2004.

(51) Int. Cl.
*G06F 19/00* (2006.01)
(52) U.S. Cl. .................. 700/245; 700/213; 700/216; 700/231; 700/232; 700/239; 318/568.11; 318/568.16; 318/568.19; 318/568.2; 318/568.21
(58) Field of Classification Search .................. 700/245, 700/213, 177, 216, 239; 318/567–568.25
See application file for complete search history.

(56) References Cited

U.S. PATENT DOCUMENTS

| | | | |
|---|---|---|---|
| 2,988,984 A | 6/1961 | Eckert et al. | |
| 3,002,387 A | 10/1961 | Micheletti | |
| 3,556,342 A | 1/1971 | Guarr | |
| 3,878,967 A | 4/1975 | Joslin et al. | |

(Continued)

FOREIGN PATENT DOCUMENTS

CA    1317262    9/1989

(Continued)

OTHER PUBLICATIONS

Biomedical Technology Consulting, "05BTC—Cytocare: Automatic system for the preparation of cytostatic drugs," pp. 1-22 with translation; downloaded from Internet site www.tecnomedical.com on Aug. 14, 2006.

(Continued)

*Primary Examiner*—Khoi Tran
*Assistant Examiner*—Jonathan Sample
(74) *Attorney, Agent, or Firm*—Fish & Richardson P.C.

(57) ABSTRACT

An Automated Pharmacy Admixture System (APAS) may include a manipulator that transports medical containers such as bags, vials, or syringes about a substantially aseptic admixing chamber. In a preferred implementation, a gripper assembly is configured to substantially universally grasp and retain syringes, IV bags, and vials of varying shapes and sizes. In an illustrative embodiment, a gripping device may include claws configured to grasp a plurality of different types of IV bags, each type having a different fill port configuration. Embodiments may include a controller adapted to actuate a transport assembly to place a fill port of the bag, vial or syringe into register with a filling port such as a cannula located at a filling station, or be equipped with carousel transport systems that are adapted to convey bags, vials, and syringes to the admixture system and deliver constituted medications in bags, vials or syringes to an egress area.

34 Claims, 26 Drawing Sheets

U.S. PATENT DOCUMENTS

| | | |
|---|---|---|
| 3,880,211 A | 4/1975 | Gess et al. |
| 3,965,945 A | 6/1976 | Ross |
| 4,058,121 A | 11/1977 | Choksi et al. |
| 4,372,464 A | 2/1983 | Otten |
| 4,464,336 A | 8/1984 | Hiramoto |
| 4,634,424 A | 1/1987 | O'Boyle |
| 4,648,430 A | 3/1987 | Di Gianfilippo et al. |
| 4,669,599 A | 6/1987 | Dijkmeijer et al. |
| 4,699,186 A | 10/1987 | Palin et al. |
| 4,706,207 A | 11/1987 | Hennessy et al. |
| 4,730,435 A * | 3/1988 | Riddle et al. ............... 53/167 |
| 4,811,764 A | 3/1989 | McLaughlin |
| 4,829,524 A | 5/1989 | Yoshida |
| 4,835,372 A | 5/1989 | Gombrich et al. |
| 4,835,707 A | 5/1989 | Amano et al. |
| 4,842,028 A | 6/1989 | Kaufman et al. |
| 4,847,764 A | 7/1989 | Halvorson |
| 4,861,335 A | 8/1989 | Reynolds |
| 4,871,559 A | 10/1989 | Dunn et al. |
| 4,878,705 A | 11/1989 | Arnquist |
| 4,910,942 A | 3/1990 | Dunn et al. |
| 4,918,604 A | 4/1990 | Baum |
| 5,004,962 A | 4/1991 | Fonss et al. |
| 5,020,958 A | 6/1991 | Tuttobene |
| 5,034,235 A | 7/1991 | Dunn et al. |
| 5,122,342 A | 6/1992 | McCulloch et al. |
| 5,144,146 A | 9/1992 | Wekhof |
| 5,169,642 A | 12/1992 | Brinker et al. |
| 5,203,385 A | 4/1993 | Waber |
| 5,208,762 A | 5/1993 | Charhut et al. |
| 5,229,074 A | 7/1993 | Heath et al. |
| 5,267,174 A | 11/1993 | Kaufman et al. |
| 5,288,285 A | 2/1994 | Carter |
| 5,309,959 A | 5/1994 | Shaw et al. |
| 5,319,543 A | 6/1994 | Wilhelm |
| 5,324,519 A | 6/1994 | Dunn et al. |
| 5,337,919 A * | 8/1994 | Spaulding et al. ............... 221/2 |
| 5,339,421 A | 8/1994 | Housel, III |
| 5,341,854 A * | 8/1994 | Zezulka et al. ................. 141/1 |
| 5,348,585 A | 9/1994 | Weston |
| 5,363,885 A | 11/1994 | McConnell et al. |
| 5,366,896 A * | 11/1994 | Margrey et al. ............... 436/48 |
| 5,411,489 A | 5/1995 | Pagay et al. |
| 5,431,201 A * | 7/1995 | Torchia et al. ................ 141/98 |
| 5,451,528 A | 9/1995 | Raymoure et al. |
| 5,479,969 A | 1/1996 | Hardie et al. |
| 5,502,944 A | 4/1996 | Kraft et al. |
| 5,522,512 A | 6/1996 | Archer et al. |
| 5,522,804 A | 6/1996 | Lynn |
| 5,533,606 A | 7/1996 | Yuyama |
| 5,534,222 A * | 7/1996 | Kelbrick et al. ............... 422/33 |
| 5,573,042 A | 11/1996 | De Haen |
| 5,597,995 A | 1/1997 | Williams et al. |
| 5,611,051 A | 3/1997 | Pirelli |
| 5,635,394 A | 6/1997 | Horn |
| 5,660,305 A | 8/1997 | Lasher et al. |
| 5,666,410 A | 9/1997 | McLane |
| 5,680,858 A | 10/1997 | Hansen et al. |
| 5,700,998 A | 12/1997 | Palti |
| 5,713,485 A | 2/1998 | Liff et al. |
| 5,713,487 A | 2/1998 | Coughlin |
| 5,744,094 A | 4/1998 | Castberg et al. |
| 5,768,853 A | 6/1998 | Bushnell et al. |
| 5,769,086 A | 6/1998 | Ritchart et al. |
| 5,786,598 A | 7/1998 | Clark et al. |
| 5,797,515 A * | 8/1998 | Liff et al. ....................... 221/2 |
| 5,798,020 A | 8/1998 | Coughlin et al. |
| 5,805,454 A | 9/1998 | Valerino, Sr. et al. |
| 5,832,447 A | 11/1998 | Riekr et al. |
| 5,839,836 A | 11/1998 | Yuyama et al. |
| 5,848,593 A | 12/1998 | McGrady et al. |
| 5,884,273 A | 3/1999 | Sattizahn et al. |
| 5,884,457 A | 3/1999 | Ortiz et al. |
| 5,895,019 A | 4/1999 | Ibarra |
| 5,900,211 A | 5/1999 | Dunn et al. |
| 5,911,252 A | 6/1999 | Cassel |
| 5,912,818 A | 6/1999 | McGrady et al. |
| 5,948,360 A | 9/1999 | Rao et al. |
| 5,971,593 A | 10/1999 | McGrady |
| 5,993,046 A | 11/1999 | McGrady et al. |
| 6,013,918 A | 1/2000 | Bushnell et al. |
| 6,037,598 A | 3/2000 | Cicha |
| 6,048,086 A * | 4/2000 | Valerino, Sr. ................. 706/10 |
| 6,060,022 A | 5/2000 | Pang et al. |
| 6,068,156 A | 5/2000 | Liff et al. |
| 6,082,987 A | 7/2000 | Su et al. |
| 6,096,561 A | 8/2000 | Tayi |
| 6,108,588 A | 8/2000 | McGrady |
| 6,141,412 A | 10/2000 | Smith et al. |
| 6,155,485 A | 12/2000 | Coughlin et al. |
| 6,161,141 A | 12/2000 | Dillon |
| 6,181,979 B1 | 1/2001 | Murakami |
| 6,181,982 B1 | 1/2001 | Yuyama et al. |
| 6,200,289 B1 | 3/2001 | Hochman et al. |
| 6,202,004 B1 | 3/2001 | Vlerino |
| 6,202,923 B1 | 3/2001 | Boyer et al. |
| 6,203,535 B1 | 3/2001 | Barney et al. |
| 6,249,717 B1 | 6/2001 | Nicholson et al. |
| 6,249,774 B1 | 6/2001 | Roden et al. |
| 6,279,724 B1 | 8/2001 | Davis |
| 6,318,630 B1 | 11/2001 | Coughlin et al. |
| 6,343,690 B1 | 2/2002 | Britton et al. |
| 6,355,024 B1 | 3/2002 | Small et al. |
| 6,360,794 B1 | 3/2002 | Turner |
| 6,370,841 B1 | 4/2002 | Chudy et al. |
| RE37,829 E | 9/2002 | Charhut et al. |
| 6,461,568 B1 | 10/2002 | Eckhardt |
| 6,470,234 B1 | 10/2002 | McGrady |
| 6,447,442 B1 | 11/2002 | Vlerino |
| 6,564,121 B1 | 5/2003 | Wallace et al. |
| 6,566,659 B1 | 5/2003 | Clark et al. |
| 6,592,816 B1 | 7/2003 | Ebel et al. |
| 6,599,476 B1 | 7/2003 | Watson et al. |
| 6,604,903 B2 | 8/2003 | Osborne et al. |
| 6,616,771 B2 | 9/2003 | Osborne et al. |
| 6,623,455 B2 | 9/2003 | Small et al. |
| 6,673,048 B1 | 1/2004 | Duchon et al. |
| 6,722,404 B2 | 4/2004 | Osborne |
| 6,735,497 B2 | 5/2004 | Wallace et al. |
| 6,832,844 B2 * | 12/2004 | Guzorek ..................... 362/263 |
| 6,877,530 B2 | 4/2005 | Osborne et al. |
| 6,883,681 B1 | 4/2005 | Coughlin et al. |
| 6,915,823 B2 * | 7/2005 | Osborne et al. ............... 141/27 |
| 6,975,924 B2 | 12/2005 | Kircher et al. |
| 6,976,349 B2 | 12/2005 | Baldwin et al. |
| 6,986,234 B2 | 1/2006 | Liedtke |
| 6,991,002 B2 | 1/2006 | Osborne et al. |
| 7,007,443 B2 | 3/2006 | Liedtke et al. |
| 7,100,792 B2 | 9/2006 | Hunter et al. |
| 7,108,679 B2 | 9/2006 | Alchas |
| 7,117,902 B2 | 10/2006 | Osborne |
| 7,278,813 B2 | 10/2007 | Davis et al. |
| 2001/0018937 A1 | 9/2001 | Nemoto |
| 2002/0020459 A1 | 2/2002 | Baldwin et al. |
| 2002/0035412 A1 | 3/2002 | Kircher et al. |
| 2002/0146343 A1 | 10/2002 | Jenkins et al. |
| 2002/0198738 A1 * | 12/2002 | Osborne ......................... 705/2 |
| 2003/0046114 A1 | 3/2003 | Davies et al. |
| 2003/0097368 A1 | 5/2003 | Tribble et al. |
| 2004/0028553 A1 | 2/2004 | Panico |
| 2004/0034447 A1 | 2/2004 | Vollm |
| 2004/0099869 A1 | 5/2004 | Gaska et al. |
| 2004/0104243 A1 | 6/2004 | Osborne et al. |
| 2004/0154690 A1 * | 8/2004 | Osborne et al. ............... 141/27 |

| | | | |
|---|---|---|---|
| 2004/0241041 | A1 | 12/2004 | Woodworth et al. |
| 2004/0250842 | A1 | 12/2004 | Adams et al. |
| 2005/0045242 | A1 | 3/2005 | Osborne |
| 2005/0133729 | A1 | 6/2005 | Woodworth et al. |
| 2005/0224137 | A1 | 10/2005 | Tribble et al. |
| 2005/0236579 | A1* | 10/2005 | Jenkins et al. ......... 250/455.11 |
| 2005/0252572 | A1 | 11/2005 | Khan et al. |
| 2005/0252574 | A1 | 11/2005 | Khan et al. |
| 2005/0279419 | A1* | 12/2005 | Tribble et al. ................ 141/27 |
| 2006/0259195 | A1 | 11/2006 | Eliuk et al. |
| 2008/0114328 | A1 | 5/2008 | Doherty |
| 2008/0199353 | A1 | 8/2008 | Reinhardt et al. |
| 2009/0067973 | A1 | 3/2009 | Eliuk et al. |

FOREIGN PATENT DOCUMENTS

| | | |
|---|---|---|
| DE | 4 314 657 | 11/1994 |
| IT | 01316152 | 12/2000 |
| WO | WO 90/09776 | 9/1990 |
| WO | WO 94/04415 | 3/1994 |
| WO | WO 95/15142 | 6/1995 |
| WO | 97/43915 | 11/1997 |
| WO | WO 97/43915 | 11/1997 |
| WO | WO 99/29412 | 6/1999 |
| WO | WO 99/29415 | 6/1999 |
| WO | WO 99/29467 | 6/1999 |
| WO | WO 00/16213 | 3/2000 |
| WO | WO 2006/069361 | 6/2006 |

OTHER PUBLICATIONS

International Search Report, PCT/US2005/046978 dated Aug. 2, 2006, 6 pages.
"Disinfection with Flash Lamps," by A. Wekhof, PDA Journal of Pharmaceutical Science & Technology, vol. 54, No. 3, May/Jun. 2000.
"Two UV-flashlamps R&D/Labor Automated System," Advanced Pulsed UV and Corona Systems From SteriBeam GmbH, Kehl, Germany, http://www.steribeam.com/xe-labor-wt.html.
"Pulsed UV Disintegration (PUVD): a new sterilization mechanism for packaging and broad medical-hospital applications," by Dr. Alex Wekhof, Dipl-Phys. Franz-Josef Trompeter, Dipl.-Ing. Oliver Franken, The First International Conference on Ultraviolet Technologies, Jun. 14-16, 2001, Washington, D.C.
"Basic Definitions and Data for Electron Beam Sterilization," by Dr. Alex Wekhof, SteriBeam Systems, GmbH, 2005.
"Does the Engineering of the PureBright Sterilisation System Match the Pulsed Light Sterilisation Process?," by Dr. Alex Wekhof, Advanced Ultra-Fast Sterilisation from SteriBeam Systems GmbH, Kehl, Germany, http://www.steribeam.com/articles/WTPP-Rep/html.
"Industrial Automated Pulsed UV Modules," Advanced Pulsed UV and Corona Systems from SteriBeam GmbH, Kehl, Germany, http://www.steribeam.com/f-scale.puv.
Office Action in Re Exam Control No. 95/000,335; mailed Mar. 7, 2008; 31 pages.
Patent Owner's Response in Re Exam Control No. 95/000,335; filed Jun. 7, 2008, 34 pages.
Request for InterPartes Reexamination in Reexam Control No. 95/000,335; filed Jan. 11, 2008; 73 pages.
Office Action in Re Exam Control No. 95/000,334; mailed Feb. 27, 2008; 17 pages.
Request for InterPartes Reexamination in Reexam Control No. 95/000,334; filed Jan. 11, 2008; 54 pages.
Office Action in Re Exam Control No. 95/000,333; mailed Mar. 7, 2008; 36 pages.
Patent Owner's Response in Re Exam Control No. 95/000,333; filed Jun. 12, 2008, 11 pages.
Patent Owner's Response in Re Exam Control No. 95/000,333; filed Jun. 7, 2008, 38 pages.
Request for InterPartes Reexamination in Reexam Control No. 95/000,333; filed Jan. 11, 2008; 39 pages.
Office Action in Re Exam Control No. 95/000,336; mailed Mar. 11, 2008; 36 pages.
Patent Owner's Response in Re Exam Control No. 95/000,336; filed Jun. 12, 2008, 13 pages.
Patent Owner's Response in Re Exam Control No. 95/000,336; filed Jun. 7, 2008, 44 pages.
Request for InterPartes Reexamination in Reexam Control No. 95/000,336; filed Jan. 11, 2008; 97 pages.
Office Action in Re Exam Control No. 95/000,342; mailed Mar. 11, 2008; 18 pages.
Patent Owner's Response in Re Exam Control No. 95/000,342; filed Jun. 7, 2008, 33 pages.
Request for InterPartes Reexamination in Reexam Control No. 95/000,342; filed Jan. 11, 2008; 89 pages.
Office Action in Re Exam Control No. 95/000,340; mailed Mar. 21, 2008; 43 pages.
Patent Owner's Response in Re Exam Control No. 95/000,340; filed Jun. 12, 2008, 10 pages.
Patent Owner's Response in Re Exam Control No. 95/000,340; filed May 20, 2008, 39 pages.
Request for InterPartes Reexamination in Reexam Control No. 95/000,340; filed Jan. 30, 2008; 33 pages.
Third Party Comments on Patent Owner Response in Reexam Control No. 95/000,340; filed Jun. 19, 2008; 19 pages.
Patent Owner's Response in Re Exam Control No. 95/000,345; filed Jun. 23, 2008, 32 pages.
Office Action in Re Exam Control No. 95/000,345; mailed Apr. 23, 2008; 110 pages.
Request for InterPartes Reexamination in Reexam Control No. 95/000,345; filed Feb. 11, 2008; 32 pages.
"Robotic system for i.v. antineoplastic drug preparation: Description and preliminary evaluation under simulated conditions" by Dennis D. Cote and Mark G. Torchia, American Journal of Hospital Pharmacy, vol. 46, Nov. 1989.
The Written Opinion, PCT/US2005/046978 date mailed Aug. 2, 2006, 10 pages.
"Aseptic Technique Process and End-product Evaluation," Department of Pharmacy Policy, 1994, University of Kentucky Hospital, Chandler Medical Center, 4 pages.
"BD Helping all people live health lives Prefilled. Proven. Preferred. ," BD Product Literature, BD, 2000.
"Welcome to the Future. The Robotic IV Admixture System: The established wave of the future with real bottom line savings." Robotic IV Admixture System; Canada, 1992.
"Dose Systems." Pharmaceutical Journal; pp. 757, vol. 254, No. 6843; Jun. 3, 1995.
International Search Report and Written Opinion, PCT/CA2008/001613 dated Sep. 12, 2008, 10 pages.
International Search Report and Written Opinion, PCT/US06/15731 dated Jul. 29, 2008, 10 pages.
International Search Report and Written Opinion, PCT/US07/84332 dated Jul. 1, 2008, 11 pages.
International Search Report and Written Opinion, PCT/US2005/046978 dated Aug. 2, 2006, 18 pages.
International Search Report and Written Opinion, PCT/CA2008/002027 dated Feb. 25, 2009, 12 pages.
Definition of "cannulal", Webster's Third New International Dictionary, Unabridged. Copyright 1993 Merriam-Webster, Incorporated.
Kohler, et al. "Standardizing the expression and nomenclature of cancer treatment regiments," Am J Health-Svst Pharm: 1998; 55: 137-144.
Office Action in Re Exam Control No. 95/000,342; mailed Oct. 15, 2008; 28 pages.
Patent Owner's Response in Re Exam Control No. 95/000,336; filed Nov. 14, 2008, 35 pages.
Patent Owner's Response in Re Exam Control No. 95/000,342; filed Nov. 13, 2008, 14 pages.
Request for InterPartes Reexamination in Reexam Control No. 95/000,342; filed Feb. 1, 2008; 27 pages.
Third Party Comments on Patent Owner Response in Reexam Control No. 95/000,333; filed Jul. 7, 2008; 29 pages.
Third Party Comments on Patent Owner Response in Reexam Control No. 95/000,335; filed Jul. 7, 2008; 18 pages.

Third Party Comments on Patent Owner Response in Reexam Control No. 95/000,336; filed Dec. 15, 2008; 7 pages.
Third Party Comments on Patent Owner Response in Reexam Control No. 95/000,336; filed Jul. 7, 2008; 22 pages.
Third Party Comments on Patent Owner Response in Reexam Control No. 95/000,342; filed Dec. 15, 2008; 7 pages.
Third Party Comments on Patent Owner Response in Reexam Control No. 95/000,342; filed Jul. 7, 2008; 28 pages.
Third Party Comments on Patent Owner Response in Reexam Control No. 95/000,345; filed Jul. 23, 2008; 16 pages.

* cited by examiner

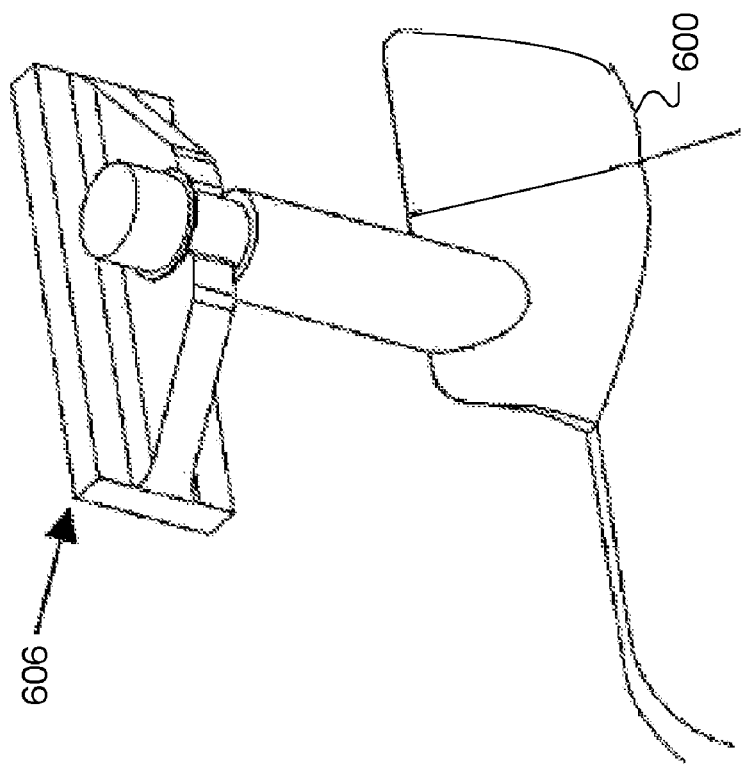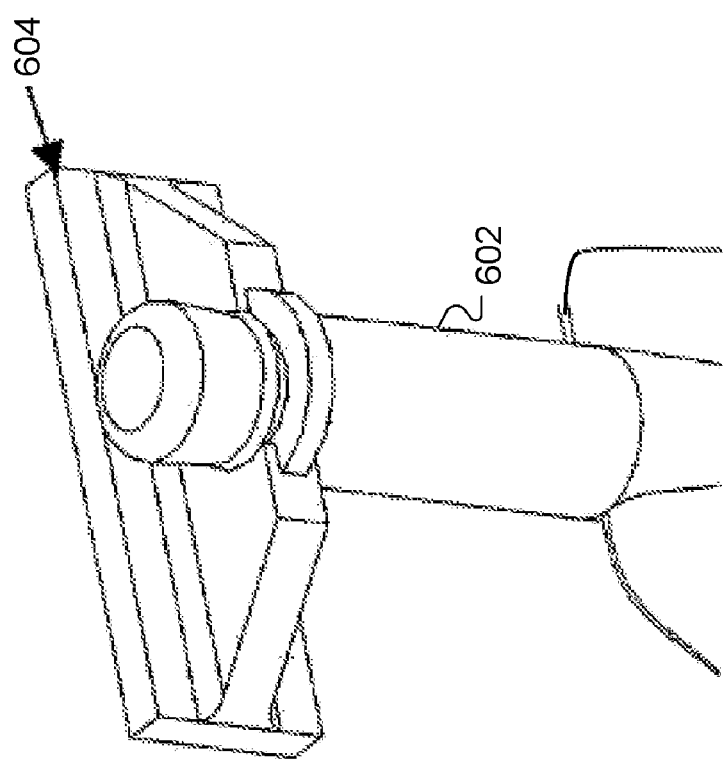
FIG. 6A

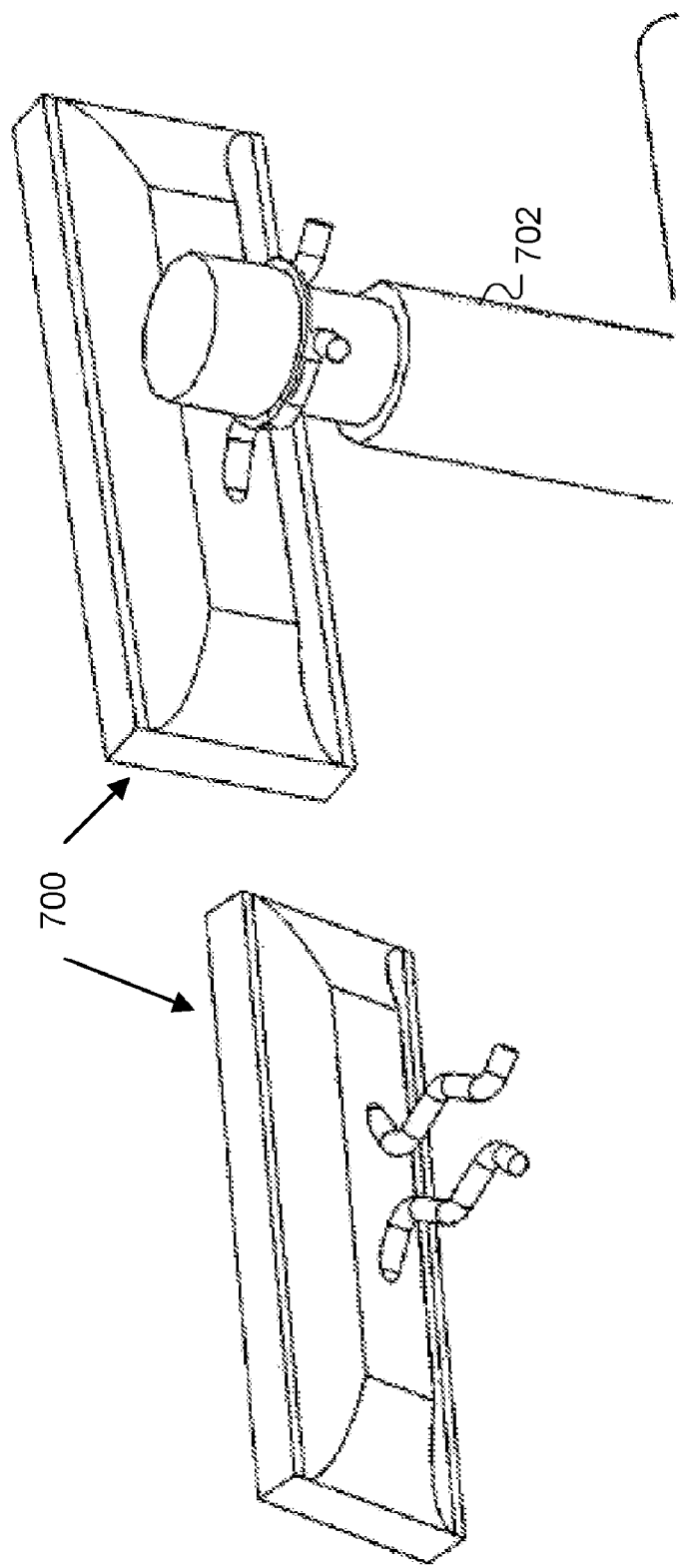

AUTOMATED PHARMACY ADMIXTURE SYSTEM (APAS)

CLAIM OF PRIORITY

This application claims priority under 35 USC §119(e) to U.S. Patent Application Ser. No. 60/638,776, entitled "Automated Pharmacy Admixture System," naming as inventors Rob, Eliuk, And Mlodzinski, and filed on Dec. 22, 2004, the contents of which are hereby incorporated by reference.

TECHNICAL FIELD

Various embodiments relate to handling medicinal containers such as syringes, vials, and/or I.V. bags.

BACKGROUND

Many medications are delivered to a patient from an intravenous (IV) bag into which a quantity of a medication is introduced. Sometimes, the medication may be an admixture with a diluent. In some cases, the IV bag contains only the medication and diluent. In other cases, the IV bag may also contain a carrier or other material to be infused into the patient simultaneously with the medication. Medication can also be delivered to a patient using a syringe.

Medication is often supplied in powder form in a medication container or in a vial. A diluent liquid may be supplied for making an admixture with the medication in a separate or diluent container or vial. A pharmacist may mix a certain amount of medication (e.g., which may be in dry form such as a powder) with a particular amount of a diluent according to a prescription. The admixture may then be delivered to a patient.

One function of the pharmacist is to prepare a dispensing container, such as an IV bag or a syringe, that contains a proper amount of diluent and medication according to the prescription for that patient. Some prescriptions (e.g., insulin) may be prepared to suit a large number of certain types of patients (e.g., diabetics). In such cases, a number of similar IV bags containing similar medication can be prepared in a batch, although volumes of each dose may vary, for example. Other prescriptions, such as those involving chemotherapy drugs, may require very accurate and careful control of diluent and medication to satisfy a prescription that is tailored to the needs of an individual patient.

The preparation of a prescription in a syringe or an IV bag may involve, for example, transferring fluids, such as medication or diluent, among vials, syringes, and/or IV bags. IV bags are typically flexible, and may readily change shape as the volume of fluid they contain changes. IV bags, vials, and syringes are commercially available in a range of sizes, shapes, and designs.

SUMMARY

An Automated Pharmacy Admixture System (APAS) may include a manipulator that transports medical containers such as bags, vials, or syringes about a substantially aseptic admixing chamber. In a preferred implementation, a gripper assembly is configured to substantially universally grasp and retain syringes, IV bags, and vials of varying shapes and sizes. In an illustrative embodiment, a gripping device may include claws configured to grasp a plurality of different types of IV bags, each type having a different fill port configuration. Various embodiments may include a controller adapted to actuate a transport assembly such that a fill port of the bag, vial or syringe is placed into register with a filling port such as a cannula located at a filling station. Illustrative embodiments may be equipped with carousel transport systems that are adapted to convey bags, vials, and syringes to the admixture system and deliver constituted medications in bags, vials, or syringes to an egress area.

Various embodiments may provide one or more of the following advantages. First, the APAS system may be substantially universal in the sense that may be configured to manipulate vials, syringes, and bags and to produce admixed medications contained in vials, syringes, or bags. Second, the APAS manipulator system may be configured to handle vessels of substantially varying size and shape, such as IV bags from different suppliers or syringes of varying diameter, length, and configuration. Third, the transport system may similarly be substantially universal in the sense that it may be configured to convey bags, syringes, and vials to the manipulator system and to convey admixed bags, syringes, and vials to an egress area.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 6A-6C shows perspective views of exemplary rigid holder embodiments for registering a fill port of an IV bag.

FIG. 7 shows perspective views of exemplary compliant holder embodiments for registering a fill port of an IV bag.

Like reference symbols in the various drawings indicate like elements.

DETAILED DESCRIPTION OF ILLUSTRATIVE EMBODIMENTS

This document describes various exemplary embodiments that relate to handling IV bags, vial, and syringes.

Figure 1:
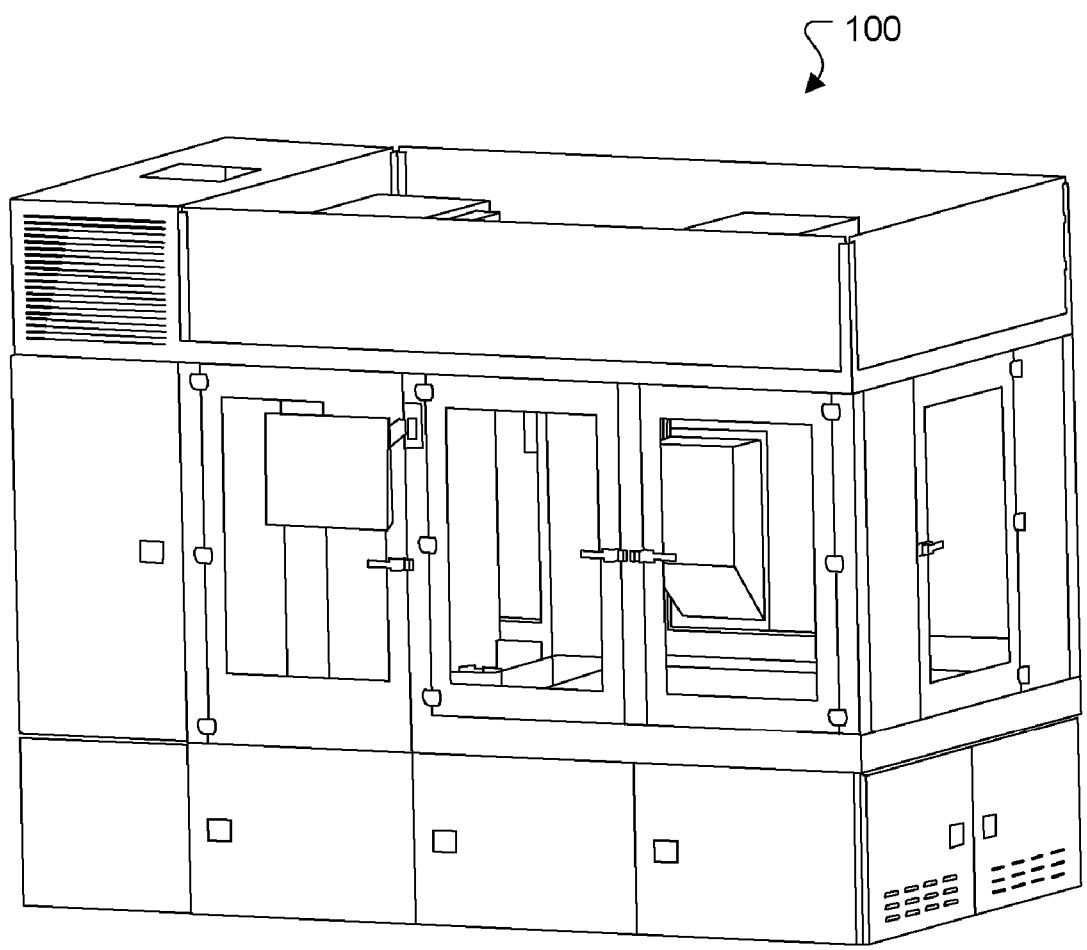
FIG. 1 shows an exemplary automated pharmacy admixture system (APAS).

FIG. 1 shows an exemplary device used within a hospital pharmacy environment, an Automated Pharmacy Admixture System (APAS) 100. The APAS 100 may autonomously admix syringes and IV bags using automation technologies. For example, embodiments of the APAS 100 may perform one or more operations that might otherwise be performed by pharmacy staff within a laminar airflow hood. The APAS 100 includes a robotic cell that automates the compounding and dispensing of drug doses into IV bags and/or syringes, such as those that may be prepared in hospital pharmacies. The robotic cell may use a syringe-based fluid transfer process, and may employ a robotic manipulator (e.g., a multiple degree of freedom arm) for moving drug vials, syringes, and IV bags through the cell as the medications are processed.

Figure 2:
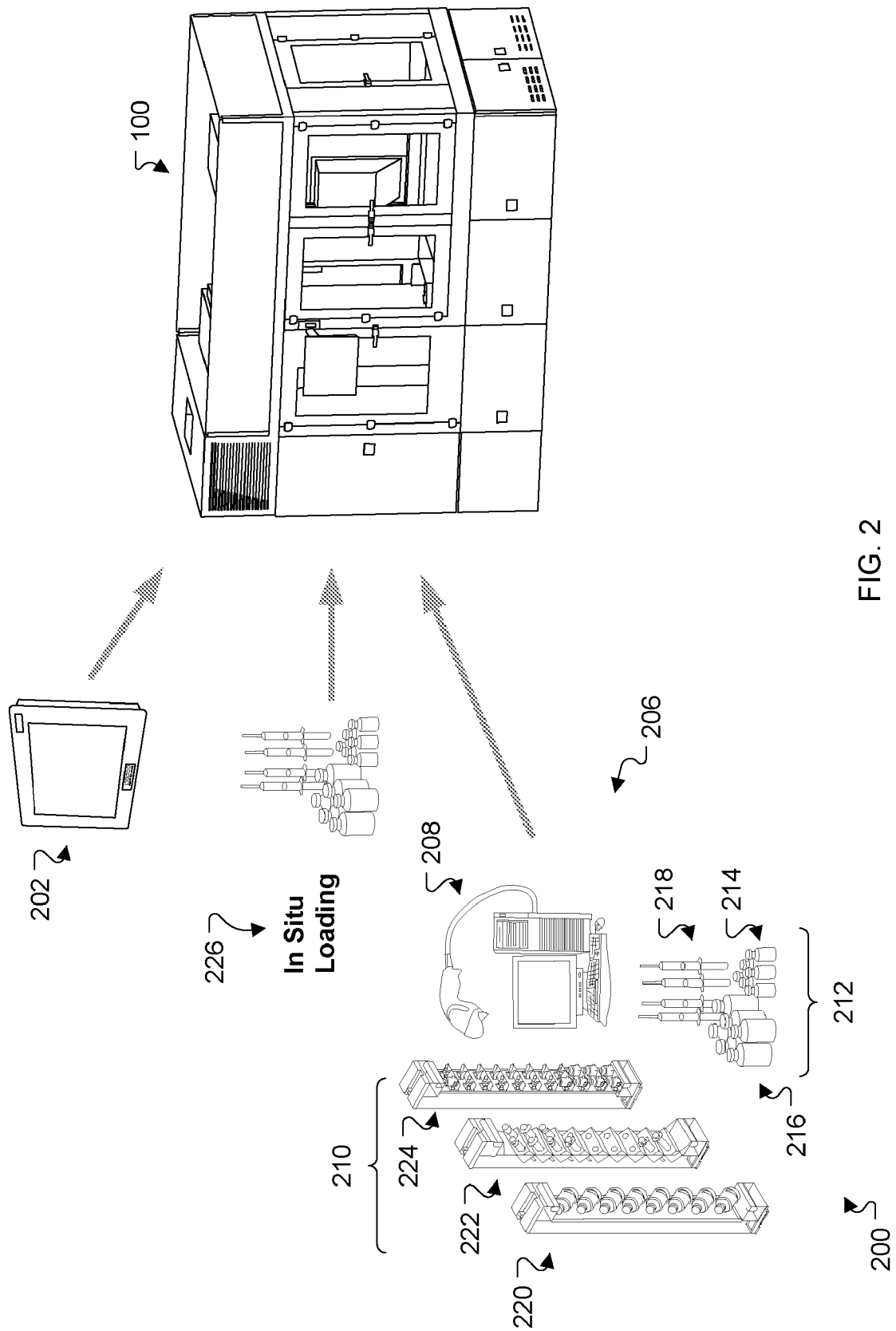
FIG. 2 shows an exemplary and aspects of an exemplary inventory system for the APAS of FIG. 1.

FIG. 2 shows exemplary equipment 200 that allows an operator to load inventory, input control information, and/or retrieve syringes and/or IV bags from the APAS 100 of FIG. 1. The APAS 100 includes a flat panel monitor 202 which may be used by an operator, for example a pharmacy technician, as a user interface to the APAS 100. The APAS 100 may include one or more flat panel monitors 202, which may be used to input control information and/or output status information, for example. In this example, the flat panel monitor 202 may also act as a control device to allow the operator, for example by touching the indicators on a touch screen, to start, stop, and pause the APAS 100. As an output device, the flat panel monitor 202 can be used in the monitoring of the status and alarm conditions of the APAS by displaying, for example, a message to the operator when a predetermined condition has occurred. As another example, an operator may use the flat panel monitor 202 to control the process of loading the APAS 100 with the drugs needed to perform its compounding process. The operator may use the flat panel monitor 202 as an input device, for example, to control the cleaning of the APAS 100 in a step-by-step manner. The flat panel monitor 202 may be used as an input and output device, for example, by a pharmacy technician while training the system for new drugs that are to be prepared in the APAS 100.

In conjunction with the APAS 100, a remote user station (RUS) 206 may provide inventory control, planning, and/or management and management functions. The RUS 206 may include a workstation 208, inventory racks 210, and inventory (e.g., drug containers) 212. The workstation 208 may be interfaced to the APAS 100, either directly or through a computer network (e.g., LAN, WAN, MAN, wLAN), which may be part of a hospital interface network in some implementations. The operator, for example, may use the workstation 208 to review, add to, prioritize, or amend drug orders and planned production for the APAS 100. The operator may also use the workstation 208 to plan and manage the compounding and/or dispensing of drug dosages by the APAS 100, and/or to report operations with regard to such processes. In another example, the workstation 208 may be used in APAS cell management to control the release of drug order queues to cells for the compounding process, or to monitor the APAS cell status during the compounding process. The workstation 208, and/or the APAS system 100, may include hardware and/or software for scanning identifying indicia, such a bar code, RFID tag, etc . . . , to facilitate the identification of inventory, and/or the placement of the inventory on a rack.

In this example, an operator may use the RUS 206 to coordinate the loading of inventory racks 210. The inventory racks 210 may be loaded with inventory 212, which may include vials of various sizes 214, 216, syringes 218 and/or IV bags (not shown). In this embodiment, each of the racks 210 may store only one type or size of inventory items; however, different racks may be arranged to hold inventory items of various sizes.

In some embodiments, one or more of the racks 210 may be configured to store multiple sizes and/or types of inventory items. In this embodiment, the racks 210 are arranged to store large vials 220, syringes 222, or small vials 224. Further embodiments of racks 210 for storing inventory may include racks for IV bags, and examples of such racks are described with reference to FIGS. 5 and 14, for example. Each inventory item may be manually placed within an appropriate support, which may include, for example, a retention clip, hook, shelf, bin, slot, or pocket on the rack 210.

The inventory 212 may be used as inputs to the APAS 100, supplying it with vials, syringes, and/or IV bags that may contain drugs and/or diluents needed by the system for the compounding process. The APAS 100 may output syringes and/or IV bags that have been prepared for use, for example, in dispensing drug doses to patients in a hospital, health care facility, clinic, or for distribution on an outpatient basis (e.g., in-home nurse visits).

In some implementations, the inventory racks 210 may be pre-loaded (i.e., off-line in advance) with the inventory 212 needed for input to the APAS 100. For example, pre-loaded racks of commonly used inputs (e.g., saline IV bags) may be prepared to satisfy anticipated, expected, or planned compounding production orders. Preloading may occur, for example, in an off-site warehouse where the racks, drug inventory, and container inventory may be stored. Some or all operations relating to the remote workstation may be performed in work areas that have a controlled environment, which may be a substantially aseptic environment. The computer device 208 may communicate with the APAS 100, and each may be programmed to process and/or exchange information about historical, current, and anticipated inventory, supply schedules, and demand information. The information may be used to prioritize, schedule, and order inventory to respond to and satisfy production input requirements for one or more APAS 100 systems, for example. In some cases, the APAS 100 may coordinate with a hospital inventory control system to place orders automatically, for example, to maintain a minimum level of inventory of certain inputs or outputs of the APAS 100 based on historical and expected demand information.

In some examples, the APAS 100 may be operated in a batch mode to produce some number of substantially similar outputs, such as cefazolin at a particular dose and in a particular type of syringe. In other examples, the APAS 100 may be operated to be loaded with inventory in situ 226. In situ loading may occur at substantially any time to produce a typically limited number of outputs, which may include a single dose, for example. In situ loading may involve, for example, loading inventory onto a rack in the APAS 100 without interrupting an on-going compounding process, or when the APAS 100 is in an idle mode.

In some embodiments may include two independently operable carousels. In one mode of operation, one of the carousels can be operating to deliver inventory to the processing chamber while the other carousel is being unloaded or loaded. In a further embodiment, the APAS 100 may include three or more inventory delivery systems, which may perform the same functions as the carousels described in this document. In such embodiments, one or more of the carousels may be operated to deliver inventory while one or more other carousels are being serviced or loaded/unloaded with inventory.

For example, a pharmacy technician may use in situ loading of the APAS 100 in response to a written or electronically received order from a physician for a medication that is needed quickly (which may be referred to as a stat order or an on-demand order). The APAS 100 may notify the technician what inputs need to be loaded to fulfill the order. Knowing the items needed for the stat order, the technician may load any inventory (i.e., drug vial, syringe, and/or IV bag, for example) necessary to perform the compounding and/or dispensing process in the appropriate rack(s) 210 and places the rack(s) 210 onto a carousel (not shown here) in the APAS 100. In another embodiment, the technician may load the inventory into unused locations in one or more racks that are already on a carousel in the APAS 100. The technician may input order information or instructions to configure the APAS 100 to prepare to fulfill the stat order.

In some examples, the APAS 100 may have stored in a memory or a database a recipe for compounding. In such cases, the operator may identify the recipe to be recalled from memory. In other examples, a pharmacy technician or operator may teach the APAS how to process the inventory using a software-driven user interface, for example. The APAS 100 may learn new recipes through a training mode, which may involve the user entering command information via a graphical user interface being displayed on the monitor 202. The operator may, for example, indicate locations of inventory items on a graphical map of the inventory system.

Figure 3:
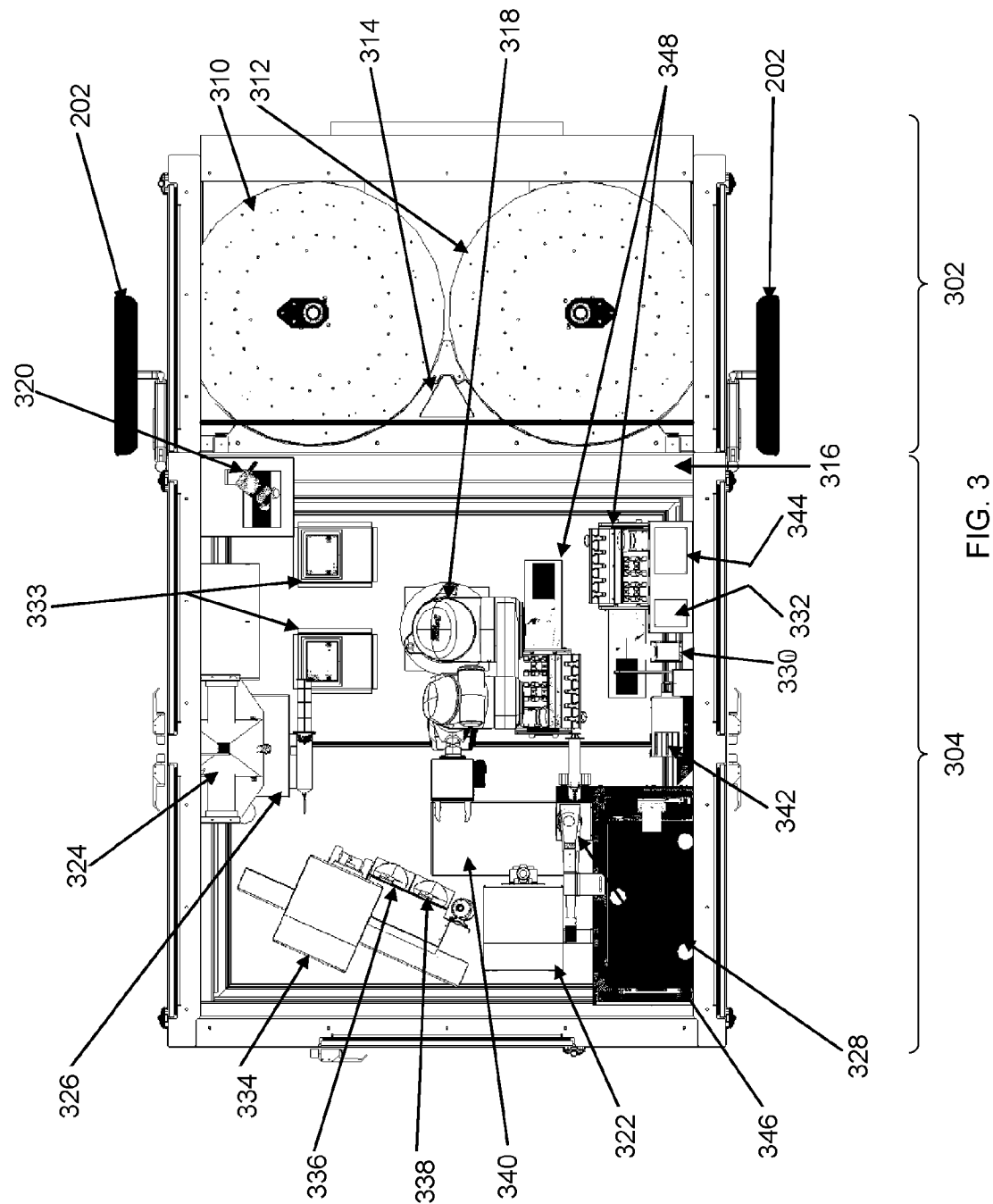
FIG. 3 shows a top cut-away view of the APAS of FIG. 1.

FIG. 3 shows a top cut-away view of the APAS of FIG. 1. The APAS 100 includes two chambers. An inventory chamber 302 is used as an inventory loading area, which can be accessed by an operator to load the APAS 100 through a loading door (not shown). A processing chamber 304 includes the compounding area in which the admixture and/or compounding processes may occur. In some embodiments, the processing chamber 304 provides a substantially aseptic environment, which may be an ISO Class 5 environment that complies with clean room standards. Mounted on the exterior of the APAS 100 are two of the monitors 202, which may serve as input/output devices as described with reference to FIG. 2.

The inventory chamber 302 includes two inventory rack carousels 310 and 312 and a temporary inventory rack 314. The temporary inventory rack 314 may be used to locate in-process drug vials that contain enough material to provide multiple doses. Each inventory rack carousel 310 may support multiple inventory racks 210. In some applications, an operator may remove one or more racks from the carousels 310, 312 and replace them with racks loaded with inventory. The racks may be loaded onto the carousels 310, 312 according to a load map, which may be generated by the operator for submission to the APAS 100, or generated by the APAS 100 and communicated to the operator. The chambers 302, 304 are separated by a dividing wall 316, an example of which is described with reference to FIG. 4.

The processing chamber 304 includes a multiple degree of freedom robotic arm 318, and the robotic arm 318 further includes a gripper that can be used, for example, to pick items from a pocket on a rack or to grasp items within the APAS 100 for manipulation. An exemplary gripper is described in further detail with reference to FIGS. 9-11. The robotic arm 318 may respond to command signals from a controller (not shown) to pick up, manipulate, or reposition inventory items within the processing chamber 304, and in or around the carousels 310, 312. The robotic arm 318 may manipulate inventory items, for example, by picking a vial, IV bag, or syringe from a rack of the carousels 310, 312 in the inventory chamber 302, and moving the item to a station in the processing chamber 304 for use in compound preparation. In some examples, the robotic arm 318 may manipulate inventory items on the carousels 310, 312 through access port 410 in the dividing wall 316. The dividing wall 316 may be substantially sealed so that a substantially aseptic environment may be maintained for compounding processes in the processing chamber 304.

According to an illustrative example, an incoming drug order from the RUS 206 involves a batch production order for syringes to be charged with individual doses of a drug that is reconstituted from a drug provided in one or more vials. The operator, for example, may preload the drug into the APAS 100 during a loading process by loading the carousel 310 with inventory racks of the drug vials, and by interfacing with the APAS 100 using the input/output device 202 to initiate, monitor, and/or control the loading process. As the APAS 100 is processing a previous order, the operator may load the carousel 312 with inventory racks of syringes, drug vials, and IV bags for the next batch production order while the APAS 100 is operating the carousel 310. Once the loading process is complete, the operator may submit the batch production process, which may begin immediately, or after other processing is completed.

To execute the batch production, in this example, the robotic arm 318 may pick a syringe from a pocket in a rack in carousel 310. The syringe in the carousel may have a needle and a needle cap. The needle cap is removed for processing in the APAS 100. The robotic arm 318 may convey the syringe to a decapper/deneedler station 320 where the needle cap is removed from the syringe/needle assembly to expose the needle. The robotic arm 318 may transfer the syringe to a needle-up syringe manipulator 322 where a dose of the drug is drawn from a vial, which was previously placed there by the robotic arm 318. The robotic arm 318 moves the syringe to the decapper/deneedler station 320 where the needle is removed from the syringe and disposed of into a sharps container (not shown here). The robotic arm 318 then moves the syringe to a syringe capper station 324, where the needleless syringe is capped. The robotic arm 318 moves the syringe to a scale station 326 where the syringe is weighed to confirm the predetermined dose programmed into the APAS. The robotic arm 318 then moves the syringe to a printer and labeling station 328 to receive a computer readable identification (ID) label that is printed and applied to the syringe. This label may have a bar code or other computer readable code printed on it which may contain, for example, patient information, the name of the drug in the syringe, the amount of the dose, as well as date and/or lot code information for the inputs. The robotic arm 318 then moves the syringe to an output scanner station 330 where the information on the ID label is read by the scanner to verify that the label is readable. The APAS 100 may report back to the RUS 206 using the hospital interface network, for use in operations planning. The syringe is then taken by the robotic arm 318 and dropped into the syringe discharge chute 332 where it is available to the pharmacy technician, for example, to be placed in inventory within the hospital pharmacy. As the process continues, there may be times during the drug order process where the robotic arm 318 removes an empty vial from the needle up syringe manipulator 322 and places it into a waste chute 333.

In another illustrative example, a syringe may be used for both as an input containing a fluid (e.g., diluent or known drug compound) to be admixed in a compounding process, and as an output containing a prepared dose suitable for delivery to a patient. Such a syringe may be needed to fulfill a special or stat order programmed into the APAS 100 via the input/output capabilities of the monitor 202, for example. In this example, the operator performs in situ loading 226 by placing the syringes to be used for both reconstitution and dosing in pockets on a rack already located on the carousel 310. The operator enters the stat order into the APAS 100. The robotic arm 318 picks the selected syringe from a pocket in the rack in the carousel 310 and moves it to the decapper/deneedler station 320, where the needle cap is removed from the syringe/needle combination, thereby exposing the needle. The syringe is then transferred by the robotic arm 318 to a needle down syringe manipulator 334. At the station 334, diluent is drawn into the syringe from a diluent supply IV bag 336 previously placed there by the robotic arm 318. The diluent supply 336 may be contained in an IV bag which is hung on the needle down syringe manipulator 334 by a clip, as shown in FIGS. 6-7. After performing an air extraction process, the details of which are described with reference to FIGS. 15A-15C, the syringe punctures the membrane of the diluent port 338 (another example of which is shown in FIG. 7) in a needle down orientation. The syringe is actuated to remove, for example, a predetermined amount of the diluent from the IV bag. The needle down syringe manipulator 334 then moves a reconstitution vial placed there previously by the robotic arm 318, under the syringe. The diluent in the syringe is transferred to the vial for reconstitution with the vial contents. The robotic arm 318 then moves the vial to the needle up syringe manipulator 322 where the appropriate amount of the reconstituted drug is drawn from the vial into an "output" syringe that was previously conveyed there by the robotic arm 318.

In another embodiment, the APAS 100 may receive a production order to prepare compounds that may involve IV bags as input inventory items or as outputs. Some IV bags may be placed on the carousel 310, 312 and used as an input that may be at least partially filled with a diluent that may be used to reconstitute drugs. The reconstituted drugs may be output in the form of charged syringes or IV bags. The operator loads racks of syringes and IV bags into the carousel 310 for use in the production order. During the production order, the robotic arm 318 picks an IV bag from a rack on the carousel 310 and moves it to the scale and bag ID station 326. At this station, the IV bag is identified by bar code or pattern matching and its weight is recorded. This may be done, for example, as an error check, and/or to positively identify the type and/or volume of diluent being used for reconstitution. As an additional verification step, the weight may be re-checked after fluid transfer operations have occurred to determine if the change in weight is within an expected range. This may detect, for example, leaks, spills, overfills, or material input errors. The robotic arm 318 moves the IV bag to a port cleaner station 340 where a pulsed ultraviolet (UV) light or other disinfecting process may be used to substantially sterilize and/or sanitize at least a portion of the IV bag port. The robotic arm 318 moves the IV bag to the needle up syringe manipulator 322 where a pre-filled syringe has been loaded. As will be described with reference to FIGS. 17A-17C, the IV bag may be inverted so that the fill port is oriented downwards for the fill process. The contents of the syringe may then be injected into the IV bag. The robotic arm 318 then conveys the IV bag to the scale station 326 where the IV bag is weighed to confirm the predetermined dose programmed into the APAS. The robotic arm 318 then moves the IV bag to a bag labeler tray station 342 where a label printed by the printer and labeling station 328 is applied to the IV bag. The robotic arm 318 may move the IV bag to the output scanner station 330, where the information on the ID label is read by the scanner to verify a readable label. The IV bag is then taken by the robotic arm 318 and dropped into the IV bag discharge chute 344 where it is available to the pharmacy technician, for example, to be placed in inventory within the hospital pharmacy.

In another embodiment, a vial may be prepared for reconstitution. During the performing of this process by the APAS 100, the vial may be identified at a vial ID station 346 where, for example, a bar coded label on the vial would be read by a scanner and that information would be supplied to the APAS 100 to identify the contents of the vial and correlate it to what is expected. In some implementations, as an alternative to or in combination with bar code scanning, the APAS 100 may employ pattern matching on the vial using optical scanning techniques. Also, in the reconstitution process, vial mixers 348 may be used to mix the vial contents with the diluent before using it for dosing.

Figure 4:
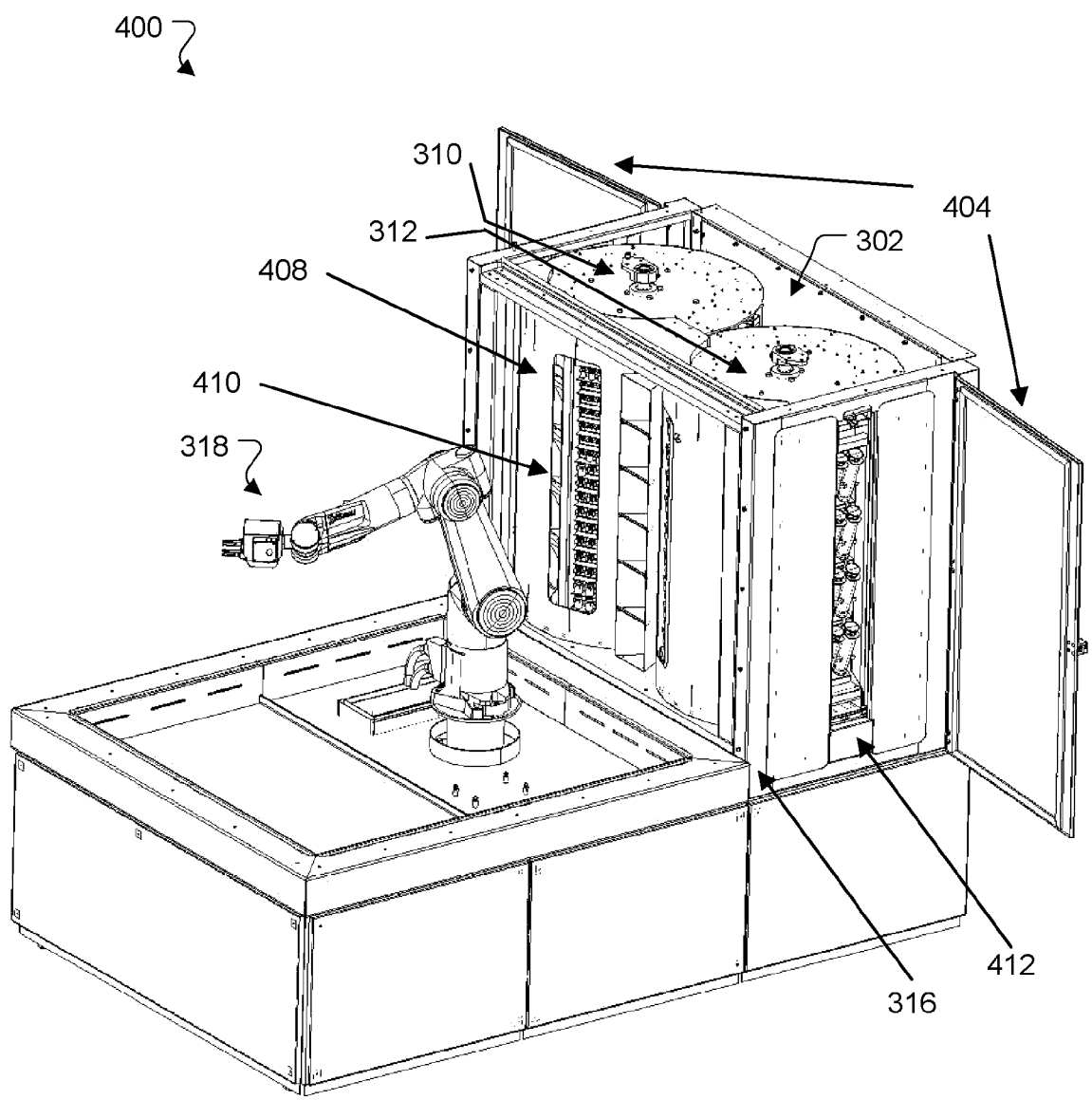
FIG. 4 is a perspective cut-away view showing details of the apparatus for handling syringes, IV bags, and drug vials in the APAS of FIG. 1.

FIG. 4 shows a perspective cut-away view 400 of an exemplary APAS, an example of which is the APAS 100, shows details of the apparatus for handling syringes and IV bags in the APAS. The handling apparatus delivers inventory, including various sizes and types of syringes, vials, or IV bags, to be grasped by the robotic arm in the processing chamber 304. An operator or technician may load/unload inventory racks that store the inventory until delivered to the robotic arm 318. In this example, the carousels 310, 312 may store syringes, vials, and/or IV bags, for example, for use in processes performed in the APAS 100. The partial view 400 of the APAS 100 is shown with the much of the processing chamber 304 removed to show the robotic arm 318 and how it can access the inventory chamber 302.

The inventory chamber 302 is shown in this embodiment with loading doors 404, which may be opened to load or remove a rack from either of the carousels 310, 312. The operator puts the APAS 100 into a loading mode giving him control of a carousel for indexing it away from the robot access position where the curved wall 408 allows the carousel rack to be close to a robot access port 410, which is in a portion of the dividing wall 316. The carousels 310, 312 may rotate to align the rack stations on the carousel with the loading doors 404 to allow rack-loading access 412. The carousel can be commanded by the operator to position any one of the rack positions in alignment with the loading access port 412. A rack that is aligned with the access port 412 can be removed and replaced with a rack containing a full load of inventory, or a rack may have its inventory replaced in situ, loading inventory into as little as a single pocket at a time. The racks can be reloaded in any combination of individual racks, including replacing all the racks at one time. At the conclusion of the rack loading, the operator may indicate via the touch screen that the APAS loading process is complete. This initiates a cycle where the carousel rotates through a 360-degree rotation to allow a barcode reader (see FIG. 14, item #1408) adjacent to the carousel to read a barcode on each of the racks. This allows the system to update the inventory data and correlate racks and inventory with carousel position information.

In this example, the dividing wall 316, which includes the curved wall 408, that separates the inventory chamber 302 from the processing chamber 304 may allow carousel 310, for example, to perform compounding processes within a substantially aseptic environment within the processing chamber 304, even while the operator is loading carousel 312. In an in situ process, for example as described in FIG. 2, the loading of carousel 312 with the stat order may be carried out while the APAS 100 is operating out of carousel 310. The dividing wall 316 may be designed to substantially minimize airflow from the inventory chamber 302 to the processing chamber 304. Similarly, an airflow restriction may be set up at the loading door 404 in the inventory chamber 302 to restrict air exchange with ambient air when the rack is in the rack loading position (i.e., aligned with the access port 412) and the door 404 is open, for example.

In one embodiment, the loading door 404 may be coupled to an interlock that requires the loading door 404 to be closed during each advance of the carousel 312 for operator safety. Such an embodiment may also help reduce uncontrolled air exchanges in or out of the inventory chamber 302 while the carousel 312 is rotated.

Figure 5:
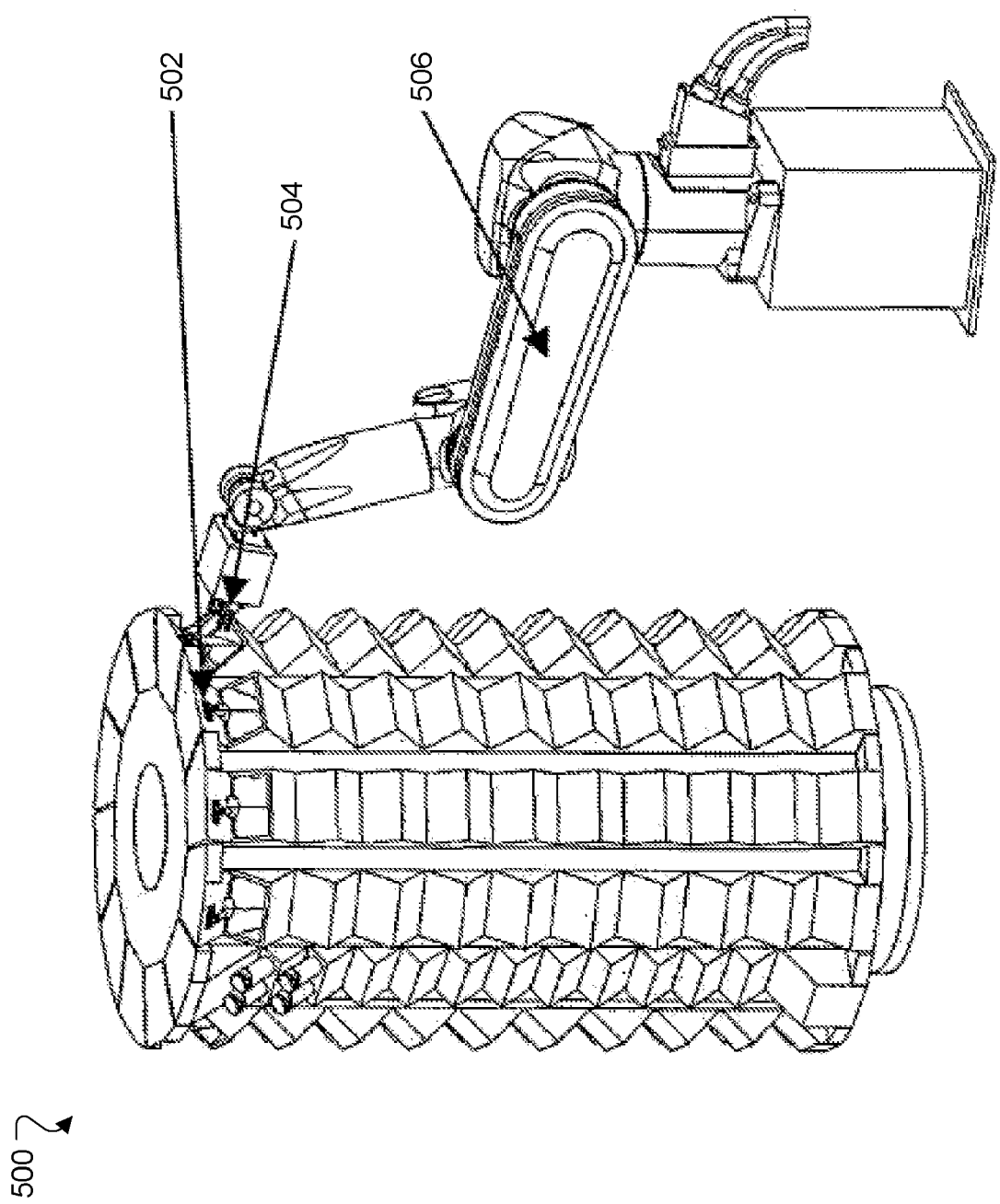
FIG. 5 illustrates an exemplary inventory system using a carousel structure with inventory racks accessible by a robotic arm in the APAS of FIG. 1.

FIG. 5 shows an exemplary inventory system 500 that expands the inventory area that the robot can access for picking inventory (e.g., drug vials, syringes, and/or IV bags) that may be processed through the cell of an automated system, such as the APAS 100, for example. This inventory system 500 includes one or more carousels 502 for mounting the inventory. The carousels 502 may be positioned within the robot travel range such that the robot can access the full height of the racks on the carousel 502. The inventory is placed in a finite number of vertical racks 504 of the type shown in FIG. 2 that are placed around the periphery of the carousel. In this example, the carousel 502 includes twelve racks, but the design can accommodate any number of racks, including partial length (e.g., half-length) racks, for example. The rack size and configuration depends on the size of the inventory items or the user requirements for inventory quantity. All of the racks can be moved within the reach range of a robot arm 506 by rotating the carousel through 360 degrees with discrete stops for each rack. Positioning of the inventory locations may involve repeatably positioning the racks on the carousel and repeatably pre-programmed stopping of the carousel rotation at each rack location.

As will be described with reference to FIGS. 12-13, the racks may be easily exchanged from the carousel for refilling. The racks are universally interchangeable in terms of position on the carousel, so that they can be removed and refilled and reinstalled in any order. FIG. 5 shows the racks as being all the same size and style, however the inventory may be separately stored on racks for each size of IV bag. Similarly, the racks can be configured for each size of syringe or combinations of syringe and size quantity.

Racks for the drug vials may also be configured to handle the full range of vial sizes. Some vial racks may be dedicated to large volume vial sizes, and some may be sectioned to handle two or more vial sizes in quantity. The diversity of the racks and the interchangeability of them allow the cell to be loaded with inventory for batch processing of a large number of doses of one type of drug or a diverse range of drugs that can be processed on demand and the mode of use can be switched from load to load of inventory. Alternately, for example, batch processing may pull inventory from one carousel and on-demand orders may pull inventory from a second carousel.

Extra racks can expand the possible range of inventory in the cell, and in situ (i.e., online) replenishment of the inventory in the cell can be accomplished with multiple carousels (two or more). Downtime of the cell may be substantially minimized by reloading one of the carousels as the other one is emptied and the cell is feeding off the other.

In this example, the carousels are substantially circular and rotate around a vertical axis. In other embodiments, the carousels may be configured to rotate around a horizontal axis, and racks may be vertically or horizontally arranged. In some embodiments, the carousel may have a cross-section that is substantially elliptical, rectangular, square, triangular, or other polygon suitable for presenting racks of inventory to a robotic arm. In some embodiments, the central portion of the carousel may rotate around an axis. In other embodiments, racks may be affixed to a belt that is continuous or segmented (e.g., chain) and supported by two or more vertical or horizontal shafts that rotate as the racks are indexed into position, or they may be supported by one or more support members that are supported by and/or extend from a rotating hoop or shaft.

The control electronics may receive a unique electronic rack identification (e.g., hall sensor, encoder, bar code reader, pattern recognition, etc . . . ) to identify the location of each rack on the carousel. This position information may be used to coordinate the rotation of the carousel to facilitate loading/unloading inventory, as well as supplying inventory to the robotic arm for processing.

In some embodiments, an APAS controller may relate the stopping position of the carousel during loading to the location of each rack. Accordingly, the controller may automatically determine and monitor the inventory content at each inventory location on the carousel. In some examples, the controller may monitor the inventory location information substantially without operator input.

In an exemplary embodiment, the APAS unit may include fill port holding and grasping features that allow IV bags of all sizes to be manifested, or registered, accurately in the inventory system so they can be picked up and moved by the robot and parked in other stations in the cell. These fill port holders may be provided to repeatably control the location of the ports so that the robot gripper can grasp the bag by the fill port and move the IV bag from station to station in the cell, and accurately plunge it onto a needle to inject the dose. With minor modifications these features can be adapted to suit IV bags from all of the major manufacturers each of which carries a unique geometry.

Figure 6B:
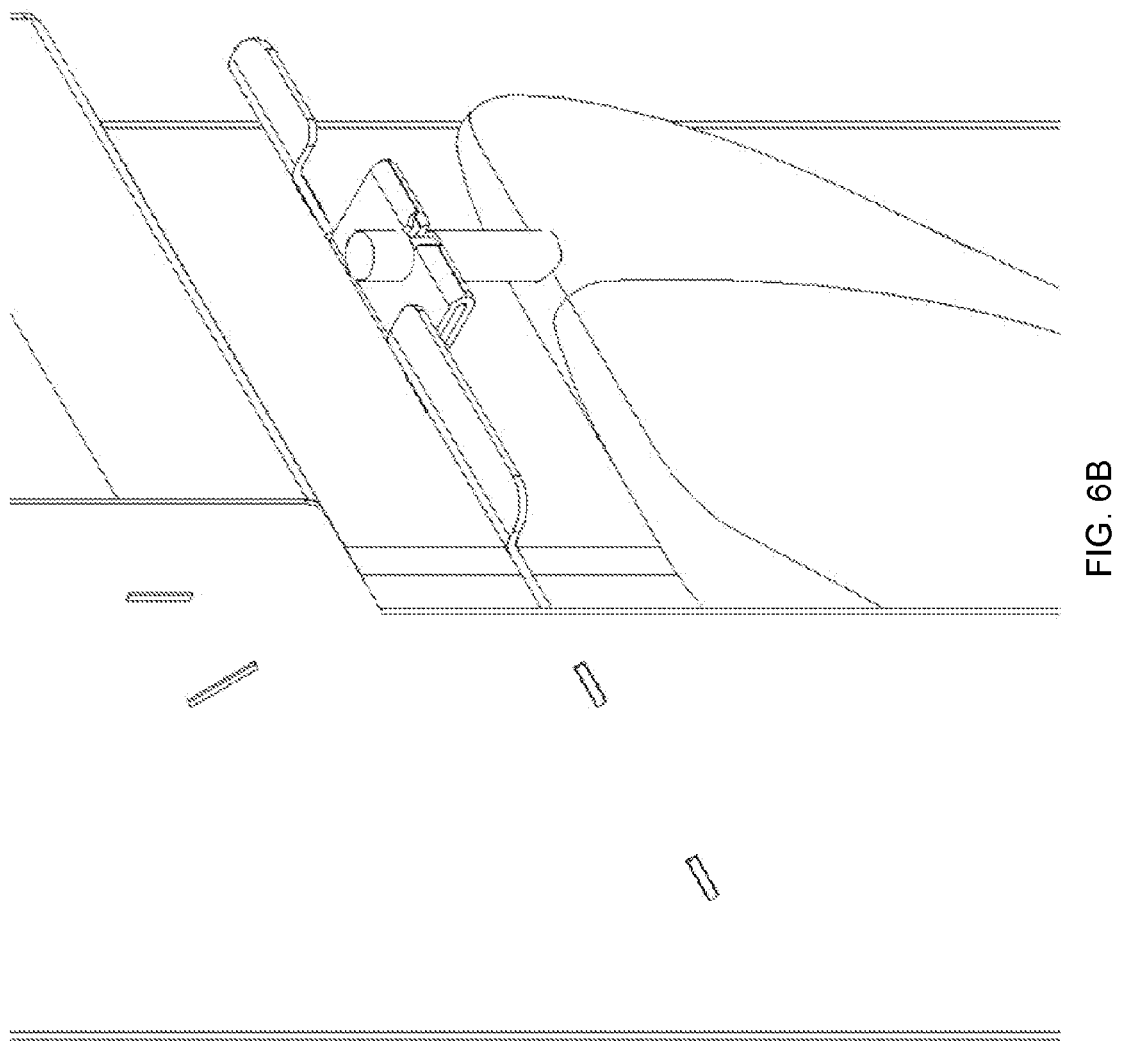
Figure 6C:
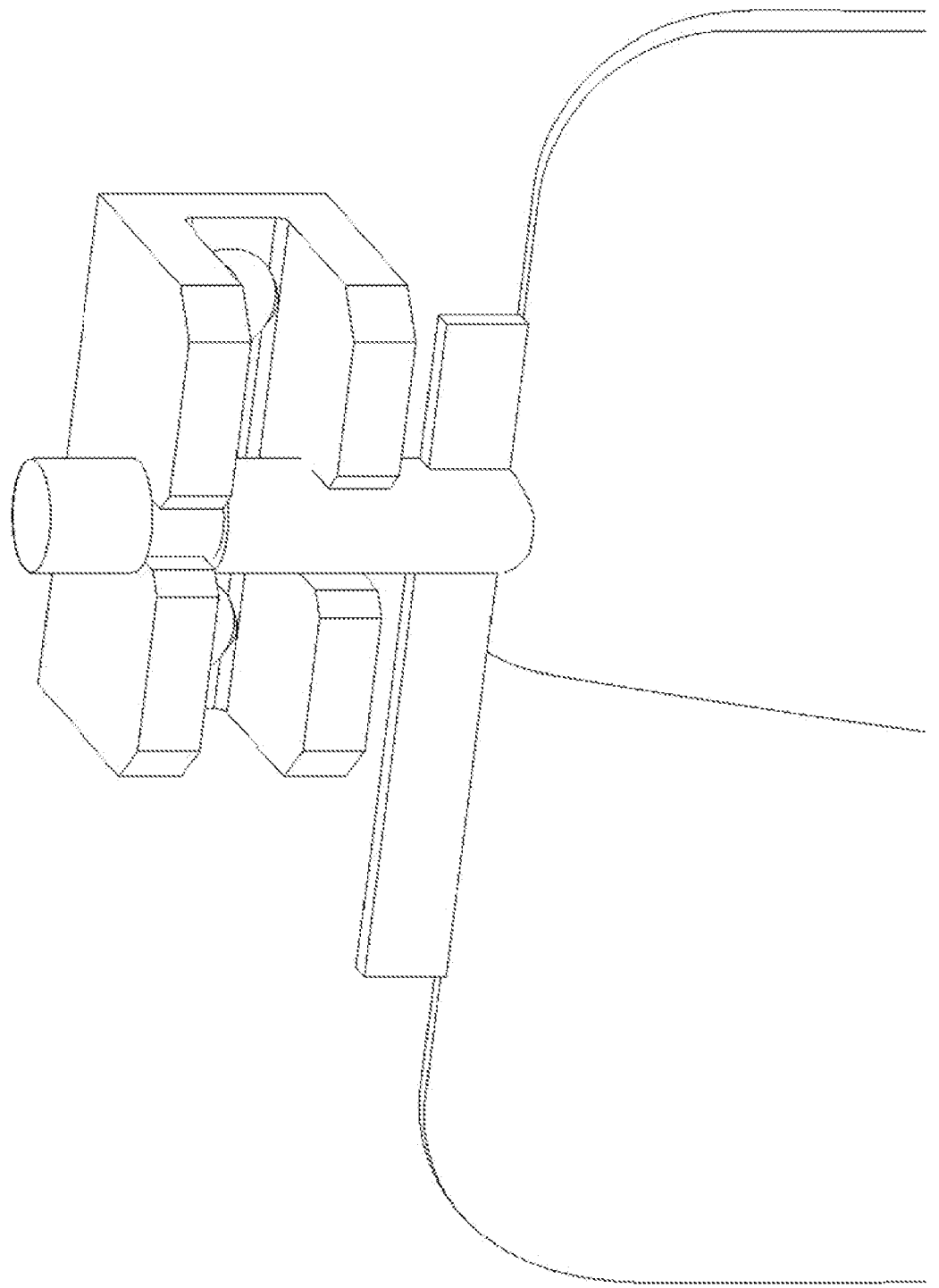

For example, exemplary means for retaining the fill ports of IV bags that are commercially available from Baxter 600 and Abbot 602 are shown in FIGS. 6A-6C. The exemplary retaining means, or retention clip, includes substantially rigid holders 604 and 606, respectively. For these holders 604, 606, the compliance of the fill port allows the fill port to be slightly deformed while inserting it into the holder.

In various embodiments, the interference between the engaging surfaces of the holder and the fill port may result in a frictional force sufficient to retain the fill port in the holder after insertion. Embodiments of the holder may be designed to pick up the bag fill port to give a unique registration on a geometrical feature of the bags that is consistent from bag to bag and throughout the full range of bag sizes from each IV bag manufacturer.

Another exemplary embodiment of a compliant holder 700 is shown in FIG. 7. That design or a variant of it would be used on bags including a fill port 702 constructed of rigid material or for high volume usage stations in the cell. An example of such a station would be on a weigh scale where every bag would be placed on the station with the robot and picked up again once or twice as it is being processed.

Figure 8:
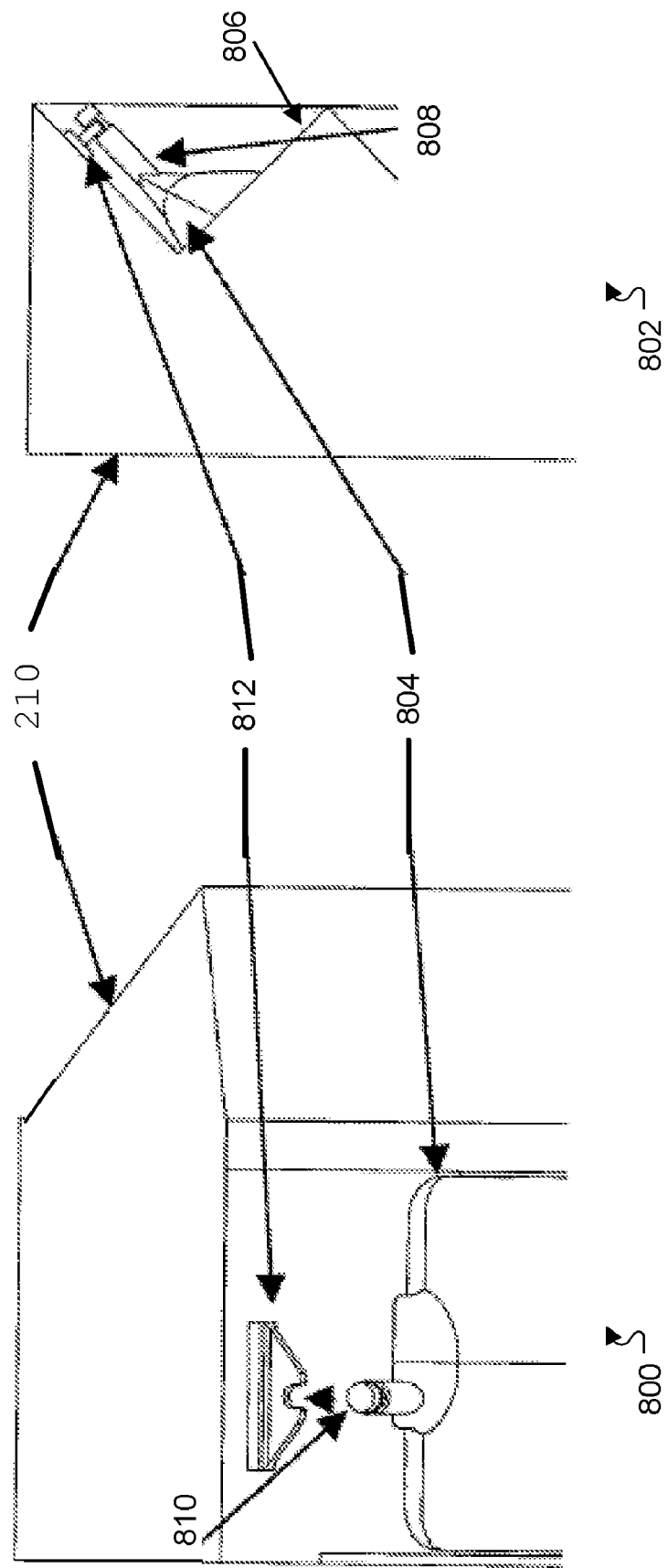
FIG. 8 shows an exemplary IV bag holder embodiment on the inventory rack of FIG. 5.

An example of the IV bag holder installed in the inventory racks 210 in FIG. 2, is shown in FIG. 8, which includes a front view 800 and a side view 802. The front view 800 and the side view 802 show how an IV bag 804, for example a Baxter bag 600, may slide into a pocket 806 in the inventory rack 210 and how fill port 810 may be fixed to the inventory rack 808 by inserting the fill port 810 into a fill port holder 812.

Figure 9:
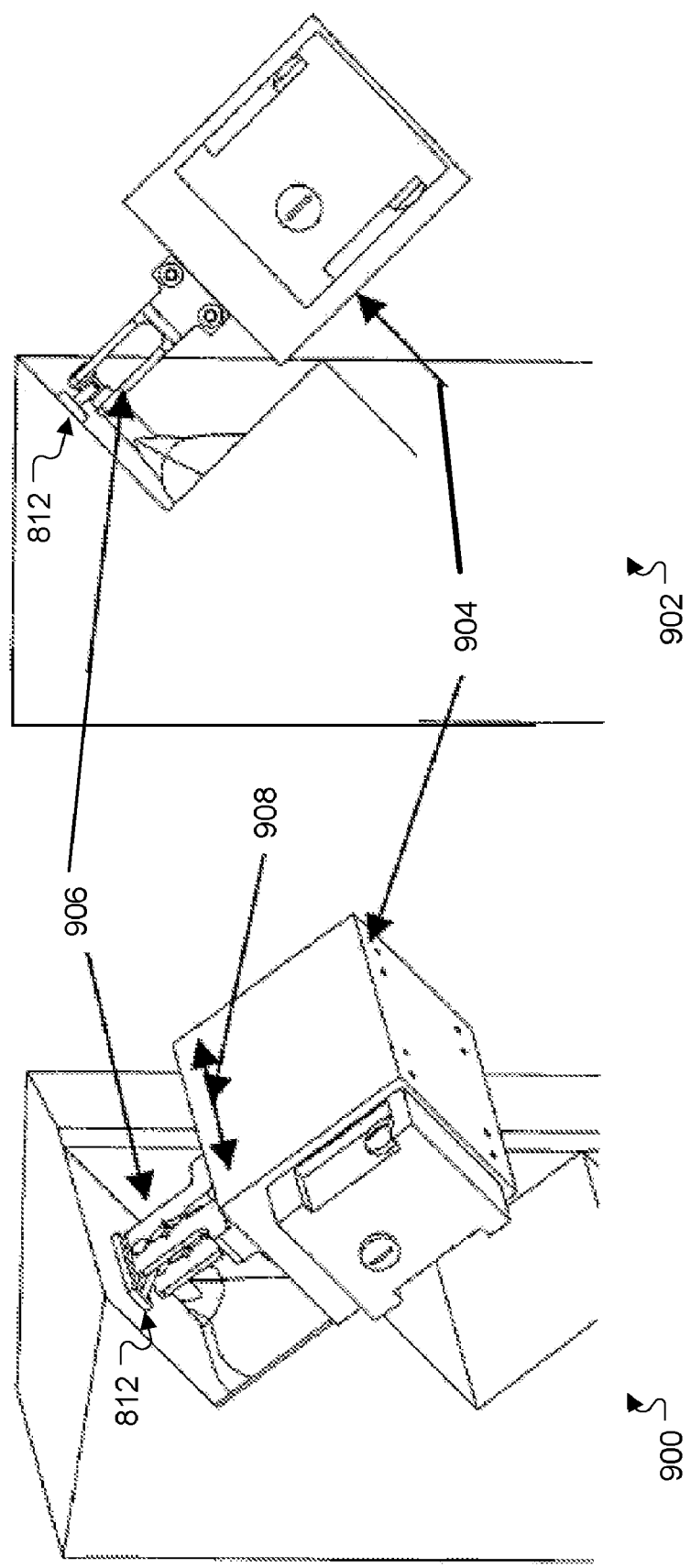
FIG. 9 illustrates a robotic arm gripper grasping an IV bag port from the holder of FIG. 8.

The robot may be programmed to pick the IV bag from the holder location by the fill port 810, as shown in a perspective view 900 and a side view 902 in FIG. 9.

In this example, the robot gripper 904 grasps the fill port 810 both above and below the bag holder 812 with two-jawed gripper fingers 906 to provide a reliable grip and provide alignment of the port with respect to the gripper axes. The robot gripper fingers move in a lateral direction 908 to grasp the fill port 810. Removal of the bag is accomplished by moving the gripper straight away from the holder (substantially parallel to the plane in which the body of the holder lies) to disengage the fill port from the holder 812. Upon disengaging the fill port from the holder 812, the robotic manipulator may then draw the bag out of the slot in a suitable motion.

Figure 10:
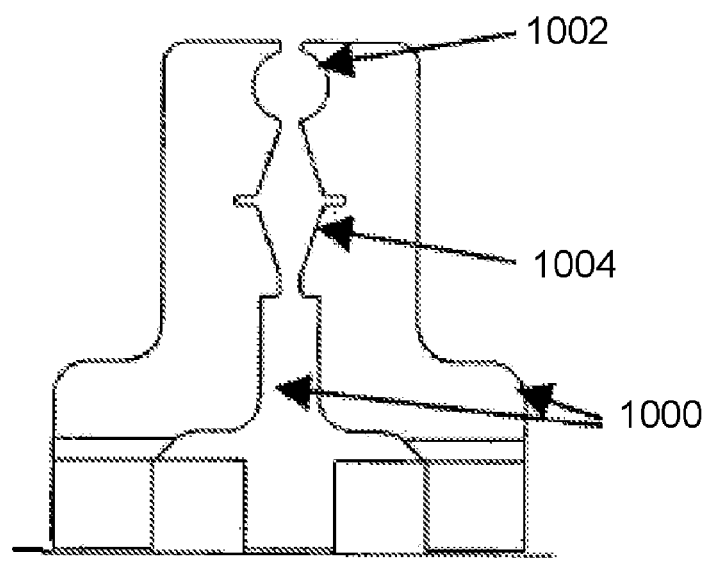
FIG. 10 illustrates an exemplary interchangeable gripper fingers for the robotic arm of FIG. 5.

As has been mentioned, the robotic manipulator may grasp the fill port of an IV bag using gripper fingers. FIG. 10 shows an exemplary set of gripper fingers 1000. The gripper fingers 1000 are designed to perform multiple operations, including handling IV bags, but also handling other items, such as vials and syringes of various sizes and types.

The gripper fingers 1000 may provide a multi-purpose design where the ends of the finger jaws have a substantially semi-circular cutout 1002 to retain or grasp the fill ports on the IV bags. The semi-circular jaw design may substantially conform to the general shape of IV bag fill ports. In various embodiments, the gripper fingers may be sized and shaped to grasp and handle various IV bag fill ports, and may be designed to support the weight of relatively heavy fluid-filled IV bags without damaging or deforming the port to an unacceptable level.

As can be seen with reference back to FIG. 9, the gripper fingers may include an upper and a lower set of opposing jaws. The spacing between the upper and lower set may be sufficient to grasp the fill port above and below the holder 812, respectively.

In some embodiments, one or more support members (not shown) may extend above and/or below the top and/or bottom surfaces of the inner diameter of the cutouts 1002. Such support members may provide additional surface area for engaging the fill port, which may distribute the force applied to the fill port across a larger area of the fill port when the gripper fingers are inserting or removing the fill port from the holder 812. Such support members may also provide additional friction, if needed, to support heavier IV bags.

To accommodate fill ports from various manufacturers, interchangeable gripper fingers may be provided. A gripper finger exchange station may be provided in the processing chamber 304 of the APAS 100, for example. To exchange one gripper finger 1000 for a different type of gripper finger based on the type of IV bag to be handled, the robotic arm may release one set of the gripper fingers 1000 in exchange for a second set having different sized cutouts 1002 to handle a different type of IV bags, for example. The releasable coupling between the gripper fingers and the robot arm may involve an electromagnet, one or more screws or bolts, and/or finger-operated spring mechanisms.

Alternatively, a universal interface to the robotic manipulator may be provided by using retention clips that have a uniform coupling interface to the robotic arm, but are adapted to adjust to, or are custom-sized for, IV bag fill ports of various types. Such clips may be attached to the fill ports outside of the APAS, and may be recycled for re-use after the IV bag has been processed by the APAS 100.

Figure 11:
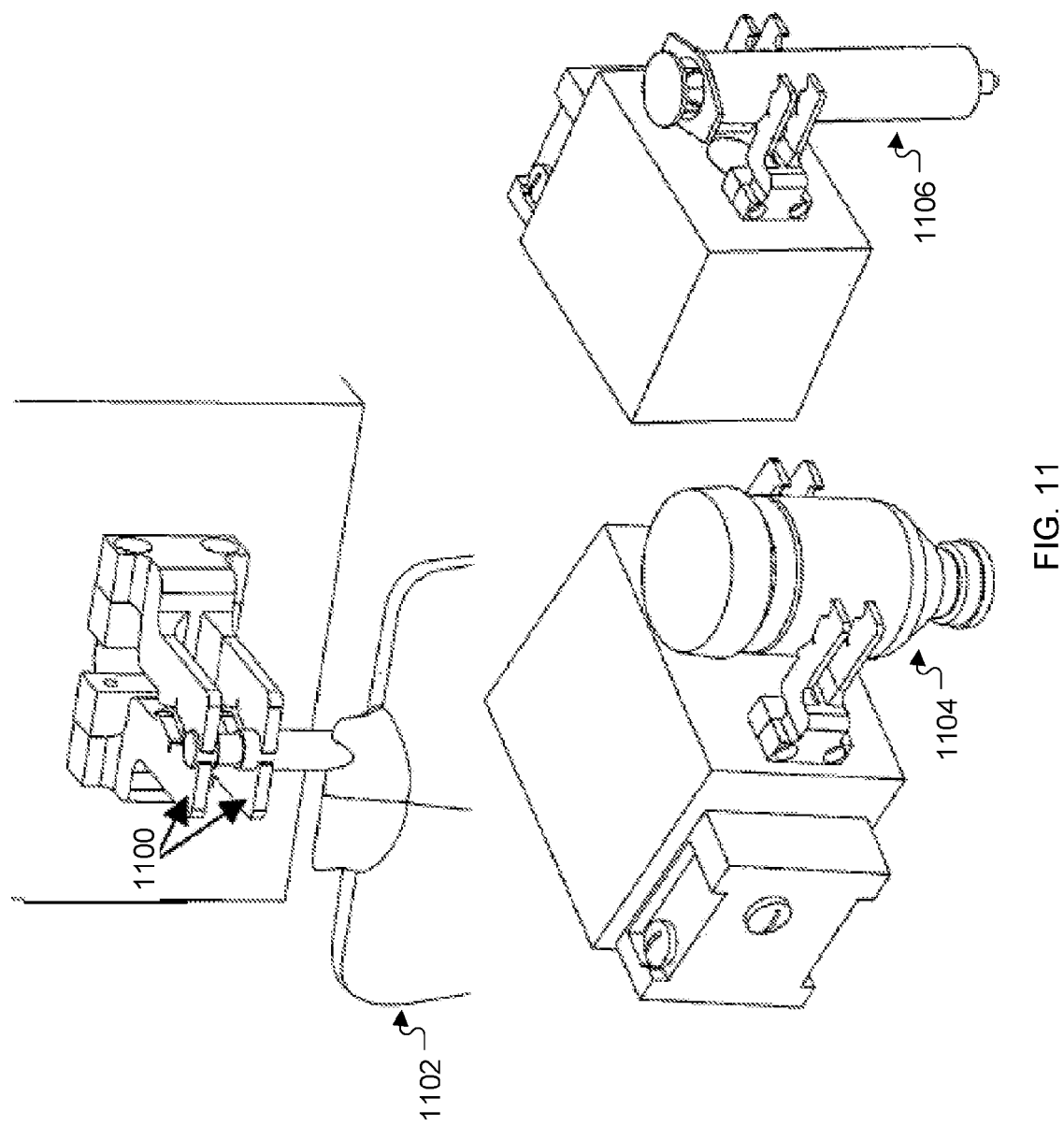
FIG. 11 illustrates possible uses of the exemplary robotic gripper fingers of FIG. 10.

A second jaw area 1004 provides a general-purpose V-shaped portion of the jaw that may be used to grasp a wide range of sizes of rigid syringes and vials as shown in FIG. 11. The dual finger design 1100 may operate the opposing jaws in a coordinated (e.g., mirror image) movements to grasp the items, for example an IV bag 1102, a vial 1104 or a syringe 1106, so that the item will substantially self-align with the gripper axes.

In some embodiments, force feedback may be used in combination with position sensing (e.g., using potentiometers, encoders, etc . . . ) to coordinate and control grasping of the gripper fingers with the robot arm movements so that the robot may grasp, retain, and release items in a coordinated fashion. Force feedback and gripper finger position sensing may be monitored to determine whether an item to be grasped is where it is expected to be, and whether it has the proper dimensions. For example, if force feedback indicates that that outer diameter of a syringe barrel is 10% larger than expected, then the APAS 100 may notify the operator of an error. As another example, if a syringe is too small for the pocket on the rack of the carousel, and is therefore tipped out an unexpected angle, then the force feedback and gripper finger position sensing may be able to detect such a condition and cause the APAS 100 to notify the operator.

The engaging surfaces of the cutout 1002 and/or the V-shaped portion 1004 may be arranged to be smooth or textured. The gripper fingers may be constructed of metal, plastic, or a combination thereof. Some embodiments may include, for example, a non-smooth textured surface, which may include rubber or other gripping material, on at least a portion of the engaging surfaces. For example, the jaw area 1004 may have a roughened surface to provide the gripper fingers 1000 with a more secure grip on the barrels of plastic syringes, for example.

In this example, the gripper fingers 1000 further include notches located at the apex of the V-shaped portion 1004. These may be used for various purposes, such as needle support and/or straightening.

FIG. 11 illustrates the flexibility of the gripper fingers 1100 for exemplary handling of various inventory items. One set of the gripper fingers 1100 can handle the IV bag 1102, a vial 1104, and a syringe 1106. As such, the gripper fingers 1100 may be used to perform a wide variety of operations in the APAS 100, for example. For example, the gripper fingers can accommodates vials and syringes having a wide range of sizes, shapes (i.e., need not be circular), weights, materials (e.g., plastic, glass, metal). The gripper fingers 1100 are also able to handle vials and syringes, for example, independent of the item's spatial orientation.

FIGS. 12A-12D show an exemplary carousel and rack system for lock loading of the rack within the carousel of the APAS 100. The inventory rack carousel, an example of which is the carousel 310 in FIG. 3, has features at its top and bottom to engage the inventory racks, and permit quick exchanges of racks on the carousel.

Figure 12A:
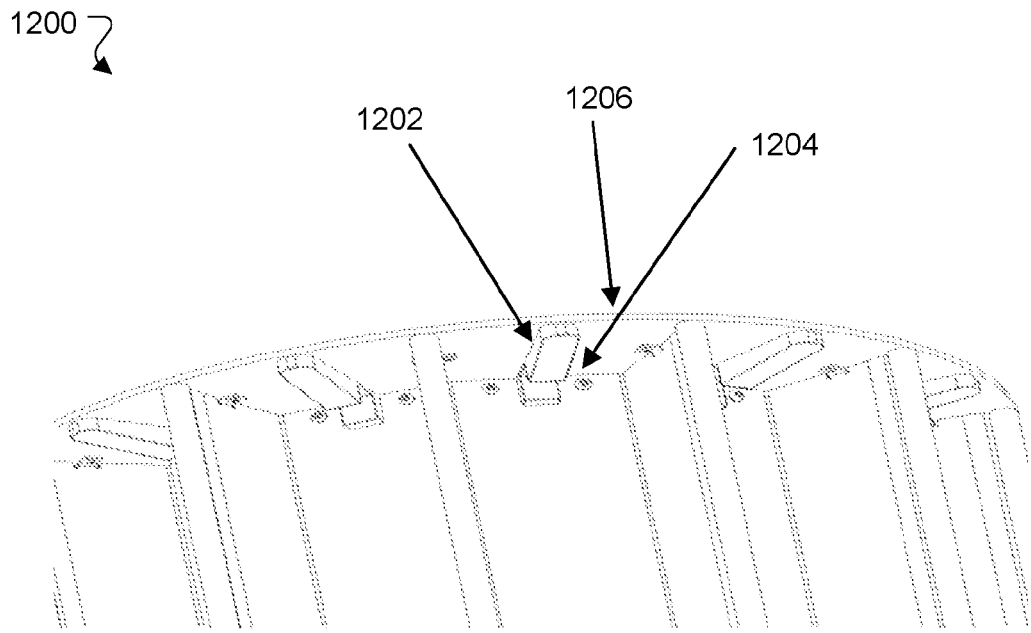
FIG. 12A-D shows the lock loading process of the rack into the carousel for the exemplary device of FIG. 1.
Figure 12B:
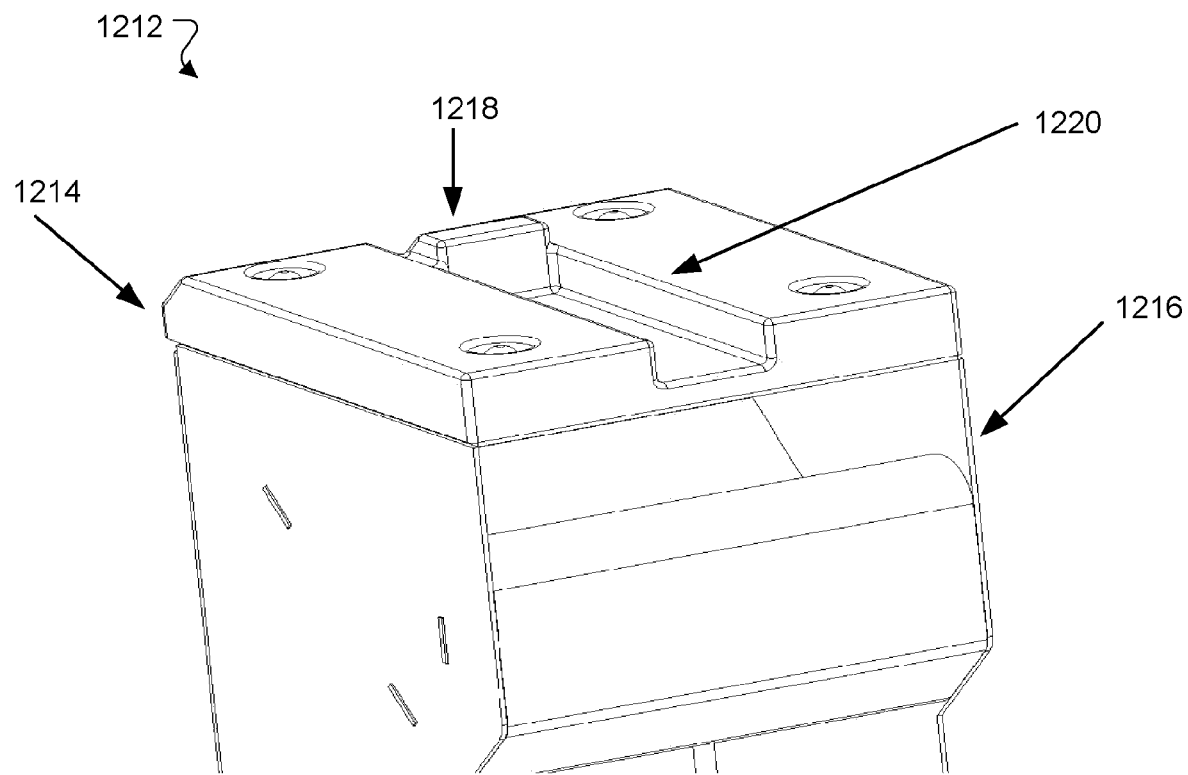

FIG. 12A shows the geometry for a carousel upper plate 1206 on a carousel 1200 to engage the racks. The carousel upper plate 1206 includes a rack alignment tongue 1202 and a rack retention slot 1204. FIG. 12B shows the geometry for an upper end of a rack 1212 that mates with and engages with the carousel 1200. The upper end of the rack 1212 has a rack upper end plate 1214 on a rack housing 1216 that provides features such as a retaining tongue 1218 and a lateral registration groove 1220 that help to engage the rack alignment tongue 1202 into the rack retention slot 1204 to provide both lateral registration and retention of the rack in the carousel 1200. This engagement is accomplished by having the lateral registration groove 1220 on the rack upper end plate 1214 engage the rack alignment tongue 1202 on the carousel upper plate 1206. The upper end of the rack 1212 is retained in the carousel by having the retaining tongue 1218 on the rack 1212 engage the rack retention slot 1204 in the rack alignment tongue 1202 on the carousel 1200.

Figure 12C:
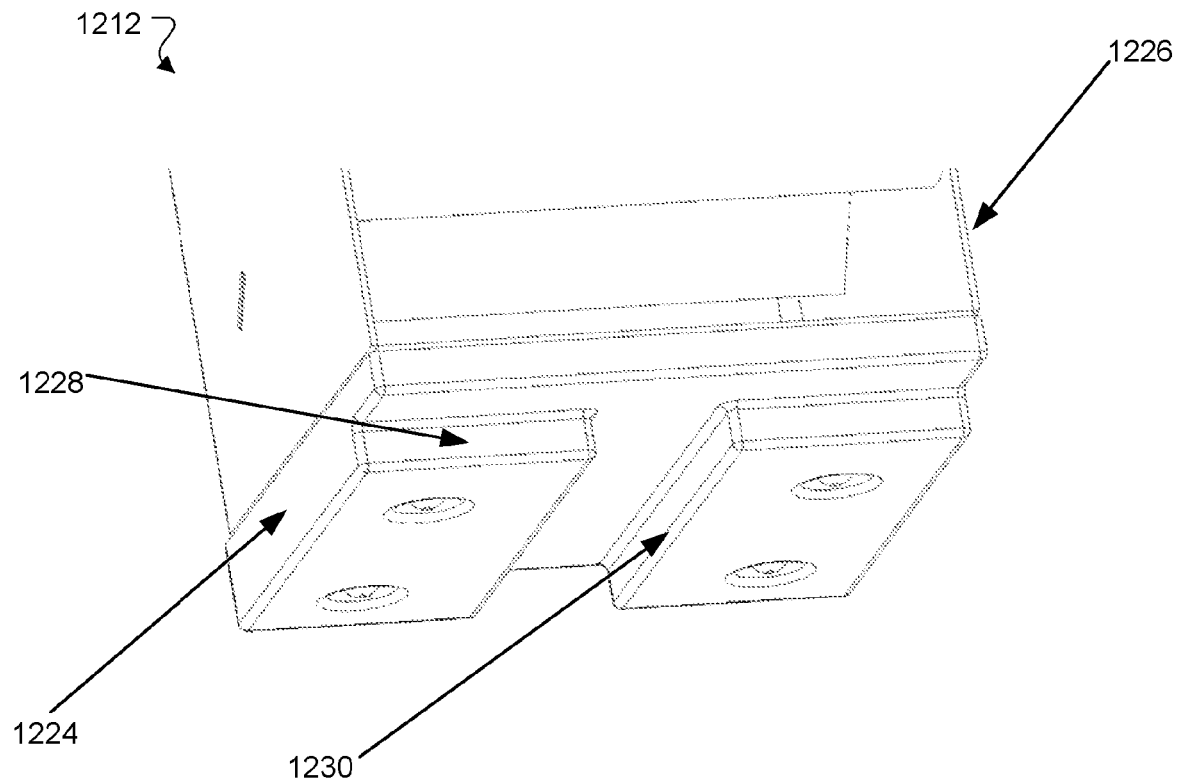
Figure 12D:
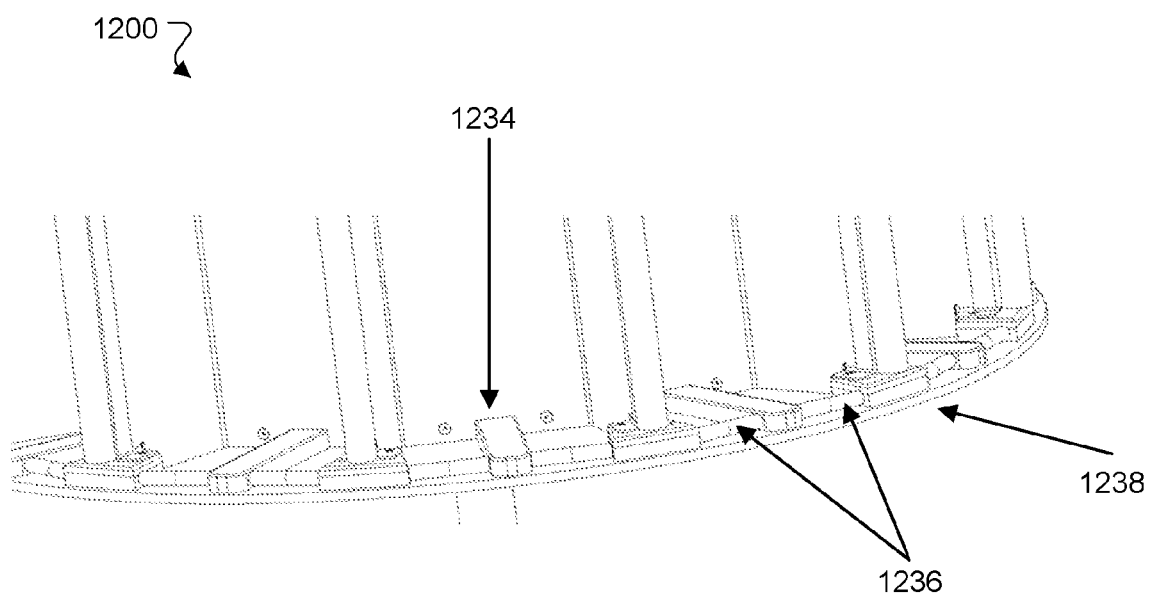

In this example, the lower end of the rack 1212 uses a similar tongue and groove alignment feature as the upper end of the rack 1212. FIG. 12D shows the geometry for a carousel lower plate 1238 on a carousel 1200 where the racks engage. The carousel lower plate 1238 includes a rack alignment tongue 1234 and rack retention rollers 1236. FIG. 12C shows the geometry for a lower end of the rack 1212 for engaging with the carousel 1200. The lower end of the rack 1212 has a rack lower end plate 1224 on a rack housing 1226 that provides features such as a retaining face 1228 and a lateral registration groove 1230 that help to engage the rack alignment tongue 1234. The rack retention rollers 1236 on the carousel lower plate 1238 are used to help guide the lower end of the rack 1212 into the carousel 1200. The lower end of the rack 1212 is engaged in the carousel 1200 by having the lateral registration groove 1230 on the rack lower end plate 1224 engage the rack alignment tongue 1234 on the carousel lower plate 1238. This provides the rack with lateral alignment and registration.

Figure 13A:
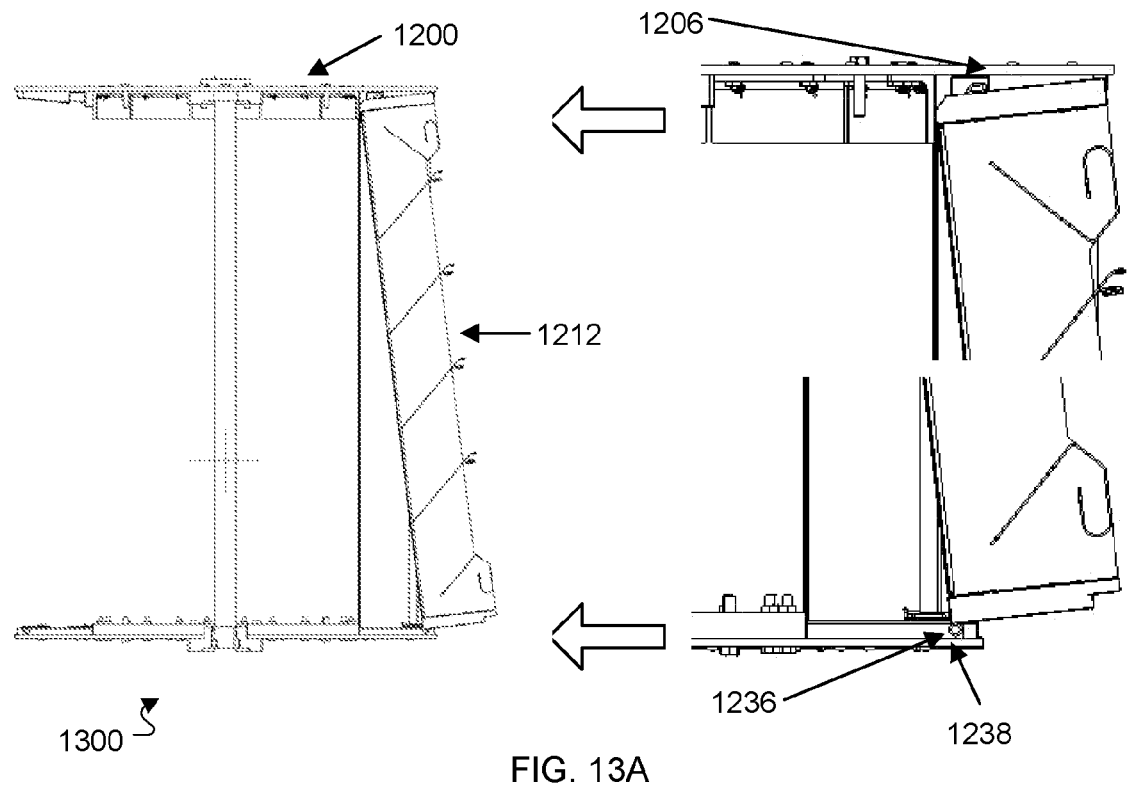
FIG. 13 A-C shows the assembly sequence of the rack into the carousel for the exemplary device of FIG. 1.
Figure 13B:
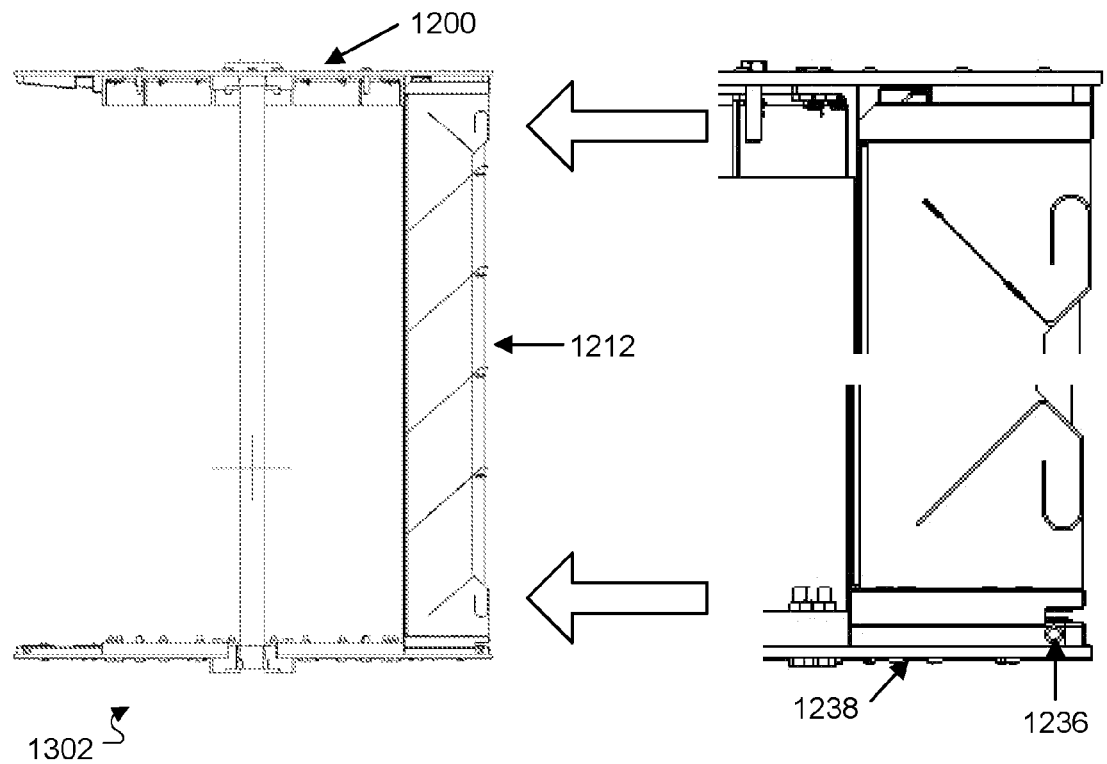
Figure 13C:
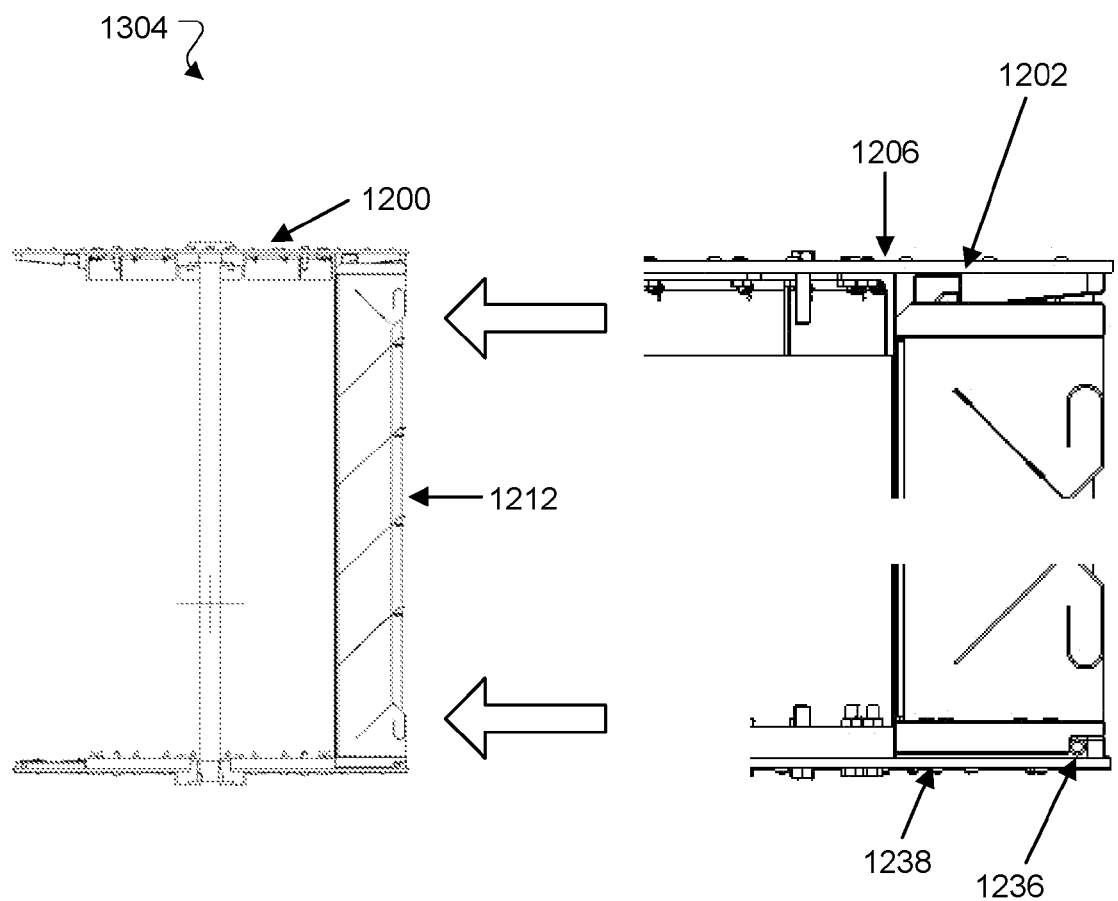

FIG. 13A-C shows an assembly sequence of loading a rack 1212 into a carousel 1200. FIG. 13A shows a first step 1300 in the assembly sequence where the rack 1212 is first engaged at the top in the carousel upper plate 1206. Next the rack 1212 can slide into the carousel 1200 by traveling over the rack retention rollers 1236 on the carousel lower plate 1238. FIG. 13B shows a second step 1302 in the assembly sequence where the rack 1212 is fully inserted into the carousel 1200. The rack 1212 has traveled over the rack retention rollers 1236 on the carousel lower plate 1238 engaging the rack alignment tongue 1234 within the lateral registration groove 1230, shown in FIG. 12. Now that the rack is fully inserted, FIG. 13C shows the last step 1304 in the assembly sequence where the rack 1212 is slid down and engages behind the rack retention rollers 1236 on the carousel lower plate 1238 and the rack alignment tongue 1202 on the carousel upper plate 1206 is engaged at the top. The rack 1212 can be lowered into the carousel 1200 so that the retaining face 1228 on the rack lower end plate 1224, as shown in FIG. 12, drops behind the rack retention rollers 1236 on the carousel lower plate 1238 and forms a captive retention in the carousel.

Removal of the rack from the carousel is substantially the reverse operation of the insertion. The rack 1212 is first lifted toward the carousel upper plate 1206, and then the lower end of the rack 1212 is rotated outwards. This disengages the retaining tongue 1218 from the alignment tongue 1202 in the carousel upper plate 1206 allowing the rack to then be free of the carousel.

In some embodiments, the carousel upper plate 1206 and the carousel lower plate 1238 may be replicated one or more times in a rack channel to provide for multiple, partial length racks instead of a single, full-length rack. Partial length racks may be provided at one or more positions on the carousel. A single partial length rack may be exchanged independently from other racks, thus avoiding exchanges of an entire rack to replace only a small portion of the inventory stored on that rack. Partial length racks may be advantageous, for example, for racks containing inventory that is physically heavy for an operator to lift and load onto a carousel. Partial length racks may also be advantageous for certain inventory that is less frequently used, for example. In some installations, a mix of partial and full length racks may be advantageous to optimize inventory management.

In another embodiment, a rack 1212 may be modified as a shell arranged to support two or more insertable mini-racks. The mini-racks may be inserted and removed from the shell in a substantially similar manner as described above with reference to FIGS. 12A-12D and 13A-13C. The shell rack may be easily exchanged to permit the full-length racks to be used as needed to provide flexible inventory management.

Figure 14:
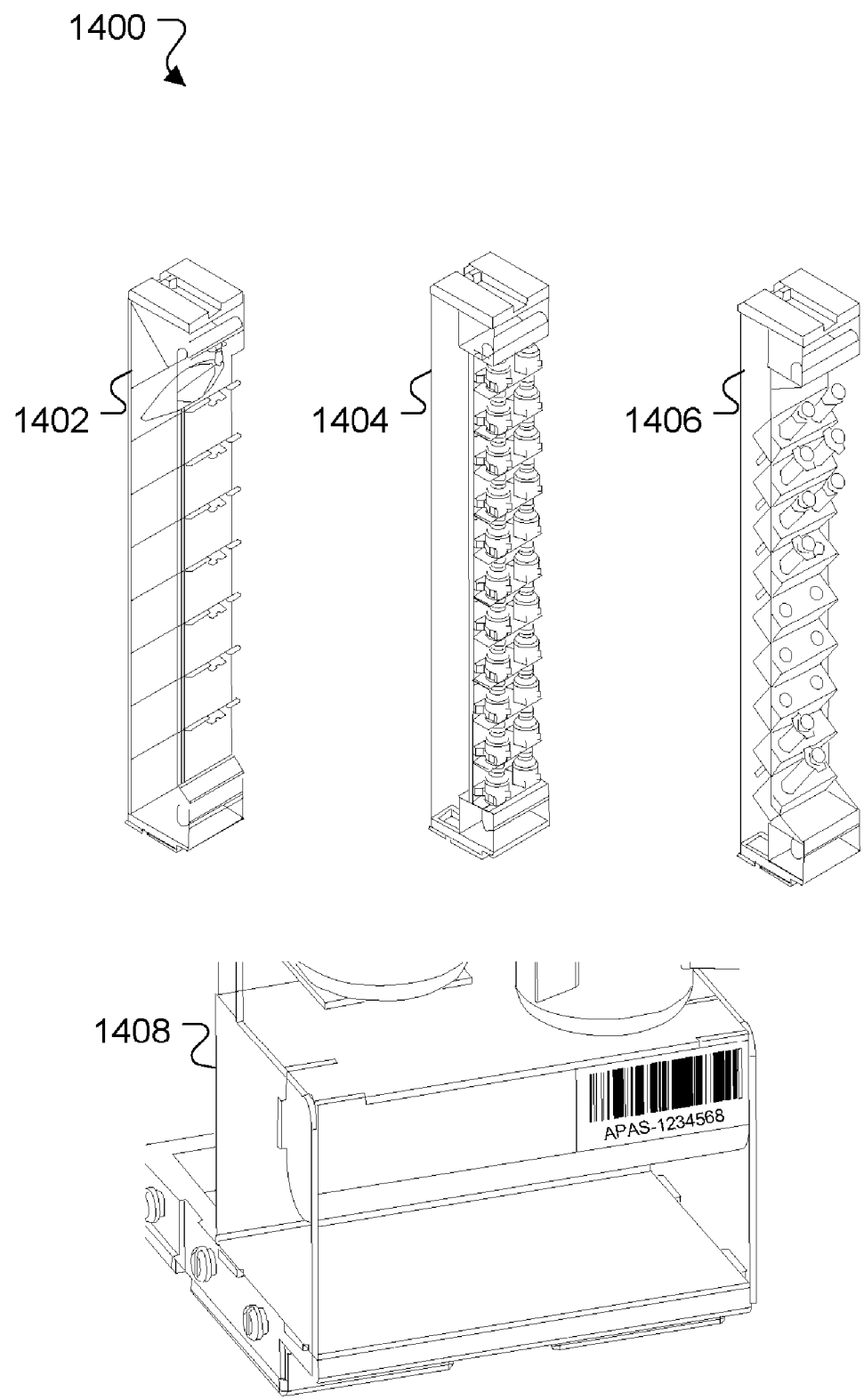
FIG. 14 shows exemplary inventory racks for use in the exemplary device of FIG. 1.

FIG. 14 shows an exemplary set of inventory rack designs 1400 that may be used to hold inventory (e.g., drug containers) 212, as shown in FIG. 2, to be used by the APAS 100 in its compounding process. The set of inventory rack designs 1400 includes, but is not limited to, three styles: a rack 1402 designed to be loaded with IV bags, a rack 1404 designed to be loaded with vials, or a rack designed to be loaded with syringes 1406. In this example, only one type of drug container is supported on each rack. However, in other examples, a single rack may contain a combination of various sizes and types of syringes, vials, and/or IV bags.

Each inventory rack style may contain multiple designs to accommodate the different sizes of each of the drug container types to be loaded on the racks. An inventory rack design may accommodate one size of a specific drug container or may accommodate a select number of sizes of a specific drug container. Examples of IV bag rack designs include, but are not limited to, a rack that can be loaded with up to four 1000 milliliter (ml) Baxter IV bags, a rack that can be loaded with up to eight 500 ml or 250 ml Baxter. IV bags, in any combination, and a rack that can be loaded with up to twelve 100 ml and 50 ml Baxter IV bags, in any combination. Examples of vial rack designs include, but are not limited to, racks that can be loaded with up to eight 100 ml vials, up to eighteen 50 ml vials and up to twenty-two 20 ml vials. Another example rack design for vials can be loaded with fifty-eight 5 ml to 2 ml, in a combination of up to thirty 5 ml to 4 ml vials and up to twenty-eight 2 ml vials. Examples of syringe rack designs include, but are not limited to, racks that can be loaded with up to eight 140 cubic centimeters (cc) Monoject syringes, up to twelve 60 cc BD or Monoject syringes, up to fourteen 30 cc BD or 35 cc Monoject syringes, up to eighteen 20 cc BD or Monoject syringes, up to thirty-three 12 cc to 1 cc BD or Monoject syringes, or any of these in combination. Monoject syringes are commercially available from Tyco medical of Massachusetts. BD syringes are commercially available from Becton Dickson of New Jersey.

Each inventory rack has an electronically readable label 1408 attached to it for identification purposes. As an example, the electronically readable label 1408 may contain, for example, a bar code which can be scanned with a bar code scanner located adjacent to the carousel 310, 312 in the inventory chamber 302. The bar code may include, or be associated with information stored in an information repository, information about the contents of the rack that can be used by the APAS, for example, to update the inventory data and correlate racks and inventory with carousel position.

In another embodiment, the drug containers may have attached to them electronically readable labels, for example bar code labels, which contain information about the amount and type of drug in the container. The drug containers may be syringes, IV bags, or vials that contain a drug or a diluent needed for a reconstitution process by the APAS. Each inventory rack may also have, for example, a bar code label at each pocket within the rack as well as a label on the rack itself, as described above. An operator, using a hand-held bar code scanner, would scan each drug container prior to placing it in the rack pocket and then they would scan the pocket label. In conjunction with the loading of the rack, the operator may scan the bar code on the rack. The data from this scan may be transferred to the APAS 100 for use in its reconstitution process. The data may indicate the exact location of a drug or diluent within a rack on a carousel.

Figure 15A:
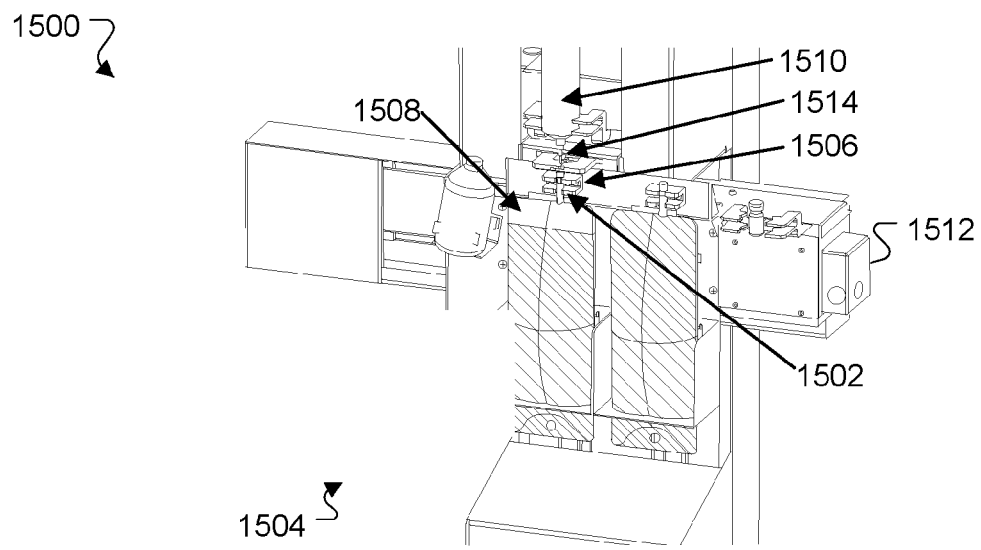
FIG. 15A-C shows an exemplary air extraction process from an IV bag used in the exemplary device of FIG. 1
Figure 15B:
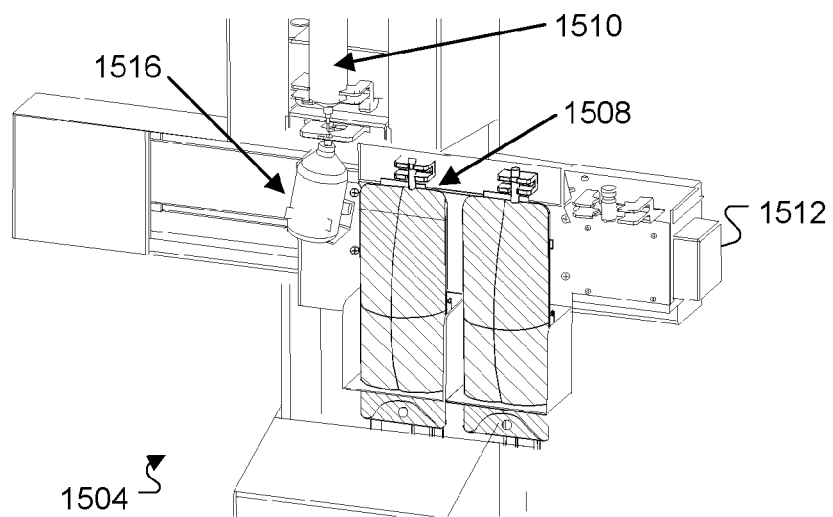
Figure 15C:
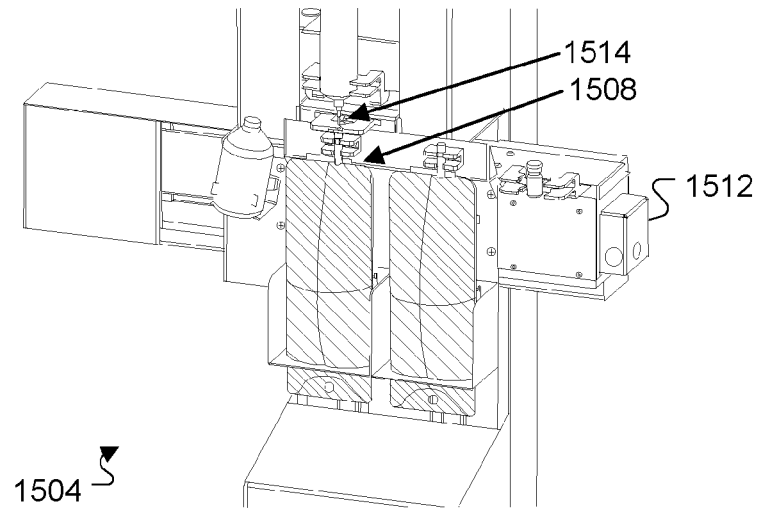
Figure 16A:
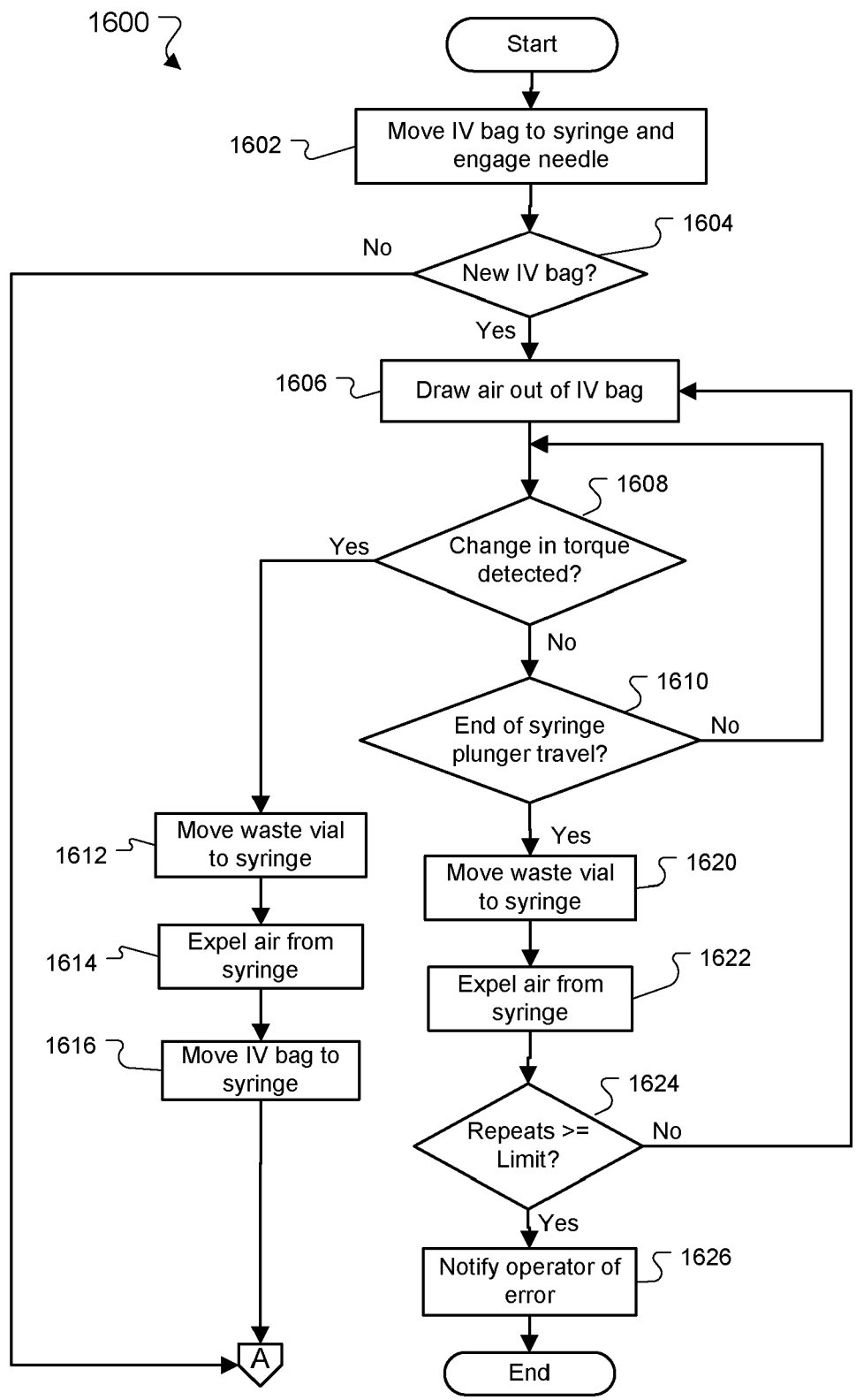
FIG. 16 is a flow chart of an exemplary method for air extraction from an IV bag used in the exemplary device of FIG. 1.
Figure 16B:
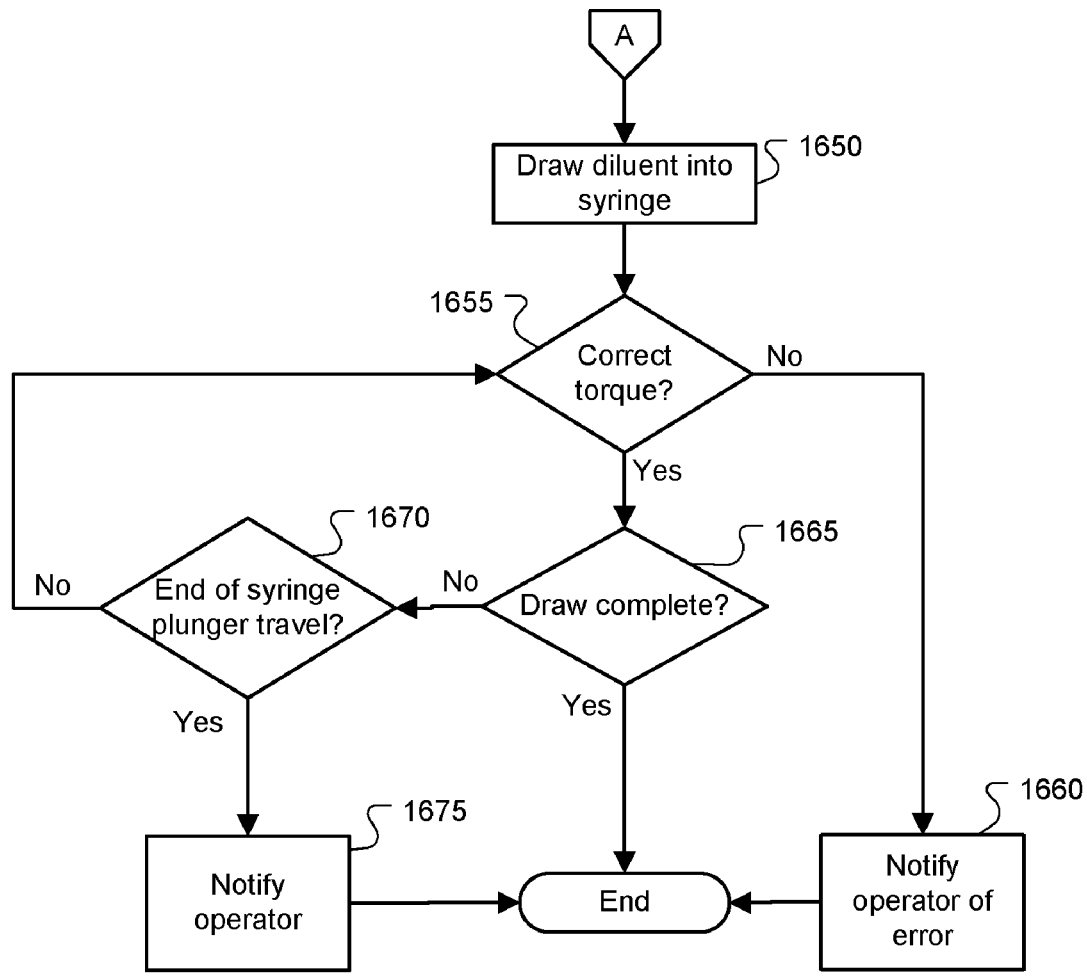

FIGS. 15A-15C illustrate apparatus and processes for extracting air and diluent from an IV bag. A process of extracting gasses from the IV bag permits the IV bag to be used for automated fluid transfer operations, and operations with a syringe in a needle down orientation in particular embodiments.

In this example, an IV bag is registered to have its fill port 1502 punctured by a needle down syringe manipulator 1504, an example of which is the manipulator 334 that was described with reference to FIG. 3. In each of FIGS. 15A-15C, two IV bags are shown as being retained by a corresponding retention clip that is holding an IV bag fill port. The retention clips may be similar to those described with reference to FIGS. 6-8.

The IV Bags as received into hospital inventory may be filled with a diluent, for example, 0.9% saline solution, sterile water or a dextrose mixture. To the extent that an IV bag to be processed in the APAS contains some gas, which may appear as a headspace in the IV bag, there is capacity to receive a drug that is injected into the IV bag. For example, a pharmacy technician using a drug filled syringe may inject its contents into the IV bag by penetrating the membrane on the IV bag port with the syringe needle. The IV bag then contains the dose needed. However, the APAS may also use an IV bag as a source of diluent in a drug reconstitution process where the drug is contained (e.g., in a liquid or dry form, such as a powder) in a vial. For example, the APAS 100 may reconstitute a drug in a vial by extracting a predetermined amount of diluent from the IV bag and injecting it into the vial.

FIG. 15A shows one exemplary stage of the reconstitution process that may occur at the needle down syringe manipulator station 1504. The needle down syringe manipulator station includes a retention clip 1506, an IV bag 1508 having the fill port 1502 that is registered by the clip 1506, a fluid transfer syringe 1510 oriented with a needle 1514 in a down position for puncturing the fill port 1502. The retention clip 1506 is mounted to an indexer 1512 that can laterally and/or vertically position the fill port 1502 relative to the needle 1514.

At the station 1504, the fill port 1502 is registered by a retention clip 1506 to permit a puncture motion relative to the needle 1514. In some embodiments, a quick puncture motion may be used to reduce the volume of air that may be entrained with the needle into the IV bag 1508. The weight of the IV bag 1508 may be supported by the retention clip 1506, although part or substantially most of the weight of the IV bag may also be supported by a horizontal shelf that the IV bag can rest on.

With the IV bag oriented so that the fill port 1502 is up, air (or other gasses) may rise toward the fill port 1502. To substantially avoid drawing gas from the IV bag 1508 into the syringe 1510 during a fluid transfer operation, a process for extracting substantially all of the air from the IV bag may be performed. The process may be terminated when all of the air has been drawn out of the IV bag 1508 and the syringe 1510 is drawing fluid. The syringe 1510 at the needle down syringe manipulator station 1504 can extract the air reliably by monitoring the syringe plunger manipulator (not shown here).

Based on the relative motion of the syringe plunger and the force required to move the plunger, a controller may be configured to determine when substantially all of the gas has been withdrawn from the IV bag 1508. The controller may receive input from sensors that may be interpreted to indicate a different force or speed, for example, that results when withdrawing air compared to withdrawing fluid. For example, if the plunger is being withdrawn at a constant speed, then the pull force on the syringe plunger (not shown) may increase measurably when substantially all of the air has been extracted and fluid starts to be withdrawn from the IV bag 1508 and into the syringe 1510. As another example, if the plunger is being withdrawn at a constant pull force or at a substantially constant excitation (e.g., terminal voltage for a DC motor), then the speed of the syringe plunger may decrease measurably when the last of the air has been extracted and fluid starts to be withdrawn from the IV bag 1508 and into the syringe 1510. Force on the syringe plunger may be monitored, for example, by strain sensors, torque sensors coupled to the motor shaft, and/or motor current. A sudden increase in current to the motor, for example, may indicate the transition from extracting air to extracting fluid. Speed may be measured or determined using various speed sensing techniques such as, for example, encoders, resolvers, multi-turn potentiometers, linear potentiometers, hall sensors, commutator noise, end-stop limit detection, limit switches, and the like, or a combination of such elements. Changes in speed may be determined from position measurements taken over time intervals.

In an alternate embodiment, the withdrawal of fluid may be detected optically, for example, by an optical sensor monitoring light passing through the fill port 1502 and/or the syringe 1510. The light intensity passing through the syringe may change when the material being extracted into the syringe changes from gas to a liquid. Optical detection may be used alone, or in combination with syringe plunger force and/or speed monitoring.

According to one implementation, a reconstitution process may be performed in the APAS 100, for example, by the robotic arm 318 placing the IV bag 1508 in the clip 1506 at the station 1504. The IV bag 1508 may hang by its fill port 1502 on the indexer 1512 of the needle down syringe manipulator station 1504. The indexer 1512 may move the IV bag 1508 to a position under the syringe needle 1514. The IV bag port 1502 may then engage the syringe needle 1514. The syringe plunger may be withdrawn so that air is drawn out of the IV bag and into the syringe 1510. The syringe plunger may be withdrawn until the change in torque, for example, is detected and, in some embodiments, for some additional time to give margin on the draw resulting in a small amount of fluid draw and/or an IV bag that is negatively pressurized relative to ambient pressure. The indexer 1512 then lowers the IV bag 1508.

FIG. 15B shows another exemplary stage of the reconstitution process that may occur at the needle down syringe manipulator station 1504. The indexer 1512 moves the IV bag 1508 with the air removed to a position that puts a waste vial 1516 under the syringe needle 1514. The waste vial 1516 is then raised by the indexer 1512 to a position where the syringe needle tip is just inside the vial neck. The syringe plunger is then driven causing air and any fluid to be expelled from the syringe 1510 into the waste vial 1516.

In FIG. 15C, the indexer 1512 is lowered and repositioned so that the IV bag 1508 is under the syringe needle 1514 and is ready to draw diluent. During a needle-down diluent draw, some small amount of air may be drawn into the syringe (e.g., micro bubbles) along with the liquid or fluid.

The needle down syringe manipulator station 1504 may be operated, for example by a programmed controller in the APAS 100, to perform an exemplary method 1600 for extracting gas from an IV bag according to the flow chart of FIGS.

16A-16B. This method 1600 may, for example, be applied in preparation for drawing diluent from the IV bag to reconstitute a drug.

When the method 1600 of this example is performed, the indexer 1512 moves the IV bag 1508 at step 1602 to a position under the syringe needle 1514, and the IV bag fill port 1502 is engaged on the syringe needle 1514 in preparation for a diluent draw. At step 1604, the APAS 100 controller determines whether or not the IV bag is considered new, i.e., whether gas has already been expelled.

If the controller determines that the IV bag is new, then, at step 1606, the controller actuates the syringe plunger to draw air out of the IV bag 1508, as described with reference to FIGS. 15A-15C. The syringe plunger manipulator 1504 may pull the syringe plunger while monitoring, for example, the torque at step 1608 for, in some embodiments, a step change indicating that the all of the air has been pulled into the syringe and fluid is now being pulled. It will also monitor at step 1610 the syringe plunger making sure it does not reach its end of travel before all of the air has been pulled from the IV bag. If the plunger has not reached the end of its travel, then step 1608 is repeated.

If, at step 1610, the plunger has reached the end of its travel, then the waste vial is moved proximate the syringe at step 1620, the air is expelled from the syringe at step 1622. In this example, the controller next determines at step 1624 if the IV bag has repeated the gas extraction process, including steps 1620-1622, more than a limit. The limit may be based on information about the IV bag, such volume, historical usage (i.e., in the APAS 100), or weight measurement, for example. If the limit is exceeded, then the controller may generate a message to notify the operator at step 1626, and the process may be terminated.

If the change in torque detected at step 1608 occurs before the end of the syringe plunger travel is reached, this indicates that substantially all air has been removed from the IV bag. At step 1612, the indexer 1512 then moves the waste vial 1516 to a position under the syringe needle 1514 at step 1612 and raises it to a position where tip of the syringe needle 1514 is inside the neck of the vial 1516. The syringe plunger manipulator 1504 actuates the syringe plunger until it stops, expelling all of the air and any liquid from the syringe at step 1614 into the waste vial 1516. The indexer 1512 next moves the IV bag 1508, which has had all of the air removed from it, to a position under the syringe needle 1514 at step 1616 to engage the IV bag port 1502 on the syringe needle 1514.

If, at step 1604, the controller determined that the IV bag is not new, or after completing step 1616, then, at step 1650, the controller may actuate the syringe plunger to start drawing a predetermined amount of diluent from the IV bag. While diluent is being drawn, the controller may, in some embodiments, monitor for the correct torque on the motor at step 1655. If the torque is incorrect, or unexpected, that may indicate a problem, so the APAS 100 may notify the operator at step 1660. However, if the torque appears to be correct, then the controller may check whether the predetermined amount of diluent has been drawn at step 1665. This may involve the controller receiving signals from a sensor, such as a slide potentiometer, for example. If the draw is complete, then the method 1600 ends. Otherwise, the controller checks whether, at step 1670, the end of the syringe plunger travel has been reached. This may be detected based on motor current, speed, plunger position, or a combination of these or similar measurements. If the end of plunger travel has not been reached, then step 1655 is repeated. If the end of plunger has been reached, the controller may send a notification to the operator of the status at step 1675, and the method 1600 ends.

The APAS, by knowing the size of the syringe and the amount of diluent it needs to draw, determines how long the syringe plunger manipulator should pull on the syringe plunger to draw the amount of fluid needed. During the draw, the syringe plunger manipulator monitors the amount of torque needed to control the syringe plunger. A step change in the torque 1620 before the draw is complete 1622 may indicate a problem and should be reported to the operator 1624 and the process stopped. An error is also indicated if the end of the syringe plunger 1628 is reached before the draw is complete. This should also be reported to the operator 1624 and the process stopped. Once the draw has successfully completed, the process ends.

In some embodiments, the controller may measure, monitor, record, and/or store information indicative of a remaining volume in a particular IV bag. This information may be used, for example, for quality control purposes, and for determining when to stop drawing diluent from the bag (i.e., when the available volume falls below a practicable level).

Figure 17A:
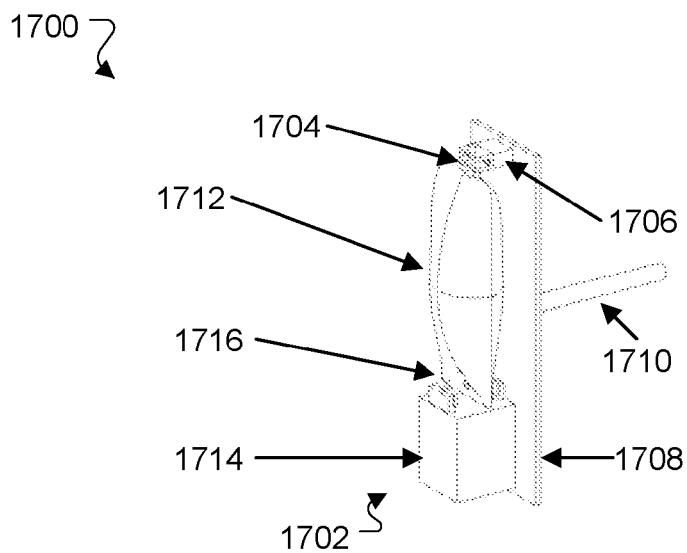
FIG. 17A-C shows an exemplary diluent bag manipulator for use in the exemplary device of FIG. 1.
Figure 17B:
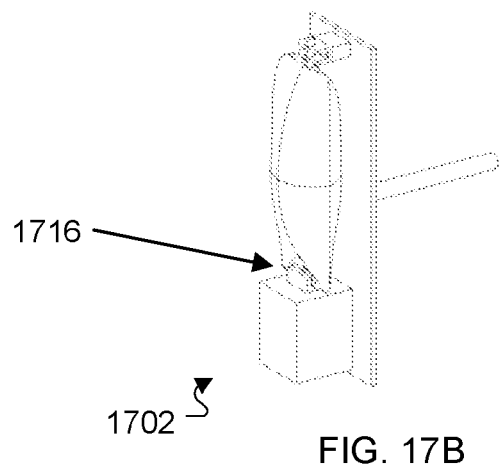
Figure 17C:
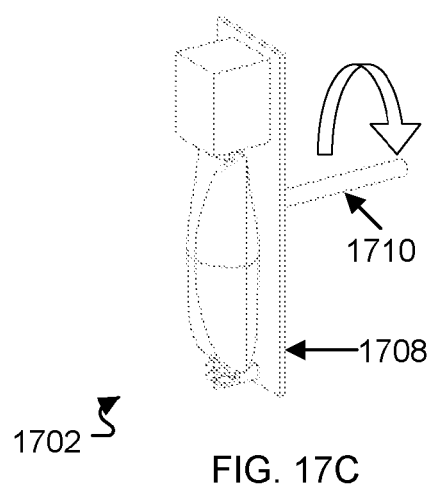

FIGS. 17A-17C show an exemplary apparatus 1700 for manipulating IV bags 1712 to be used to supply a diluent for a reconstitution process.

In FIG. 17A, an exemplary diluent bag manipulator station 1702 is provided in, for example, the APAS 100, for the purpose of manipulating IV bags containing diluent needed in a reconstitution process. A robotic arm 318, as described in FIG. 3, may convey or transport an IV bag to the station 1702. The arm may be actuated by a controller in the APAS 100 to register a fill port 1704 of the conveyed IV bag with a clip 1706, as described with reference to FIGS. 6-7, on a platen 1708. The bottom of the IV bag 1712 is placed into a gripper 1714 where gripper jaws 1716 are in the open position. Next, in FIG. 17B, the gripper jaws 1716 are closed to grasp the bottom of the bag. The IV bag 1712 is thus restrained by the closed gripper jaws on the bottom of the bag along with the top of the IV bag being secured in the IV bag clip 1706. FIG. 17C shows how the platen 1708 is rotated, for example, 180 degrees along the rotation axis 1710 to invert the IV bag to be oriented with IV bag fill port 1704 down, which may cause air in the IV bag 1712 to rise to the top. In this embodiment, diluent may be supplied, (e.g., by gravity feed or peristaltic pump) without a preparatory step of extracting the air from the IV bag 1712 before a syringe draw.

In this embodiment, the diluent bag manipulator station 1702 could be used for orienting IV bags for fluid transfer on the needle up syringe manipulator station 322, as shown if FIG. 3.

In some embodiments, the APAS 100 would have stored information (e.g., from visual inspection, weight measurement, historical information, user input, etc . . . ) about the approximate fluid volume available in the IV bag. A controller in the APAS may determine when the available volume in the IV bag has been depleted to a level below which the IV bag may be discarded, or used for another purpose.

In some embodiments, the removal of the IV bag from the diluent bag manipulator station 1702 may involve rotating the platen again by 180 degrees to re-orient the IV bag as shown in FIG. 17B. The gripper jaws may then be opened, releasing the bottom of the IV bag. The robotic arm may then grasp the IV bag by the port, as has been described, and withdraw it to remove it from the clip. The robotic arm would then place the empty bag, for example, into a waste chute 333, as shown in FIG. 3.

In another embodiment, the gripper 1714 may move in a direction to increase or decrease the distance of separation between the jaws 1716 and the clip 1706 to allow for different size bags.

Figure 18:
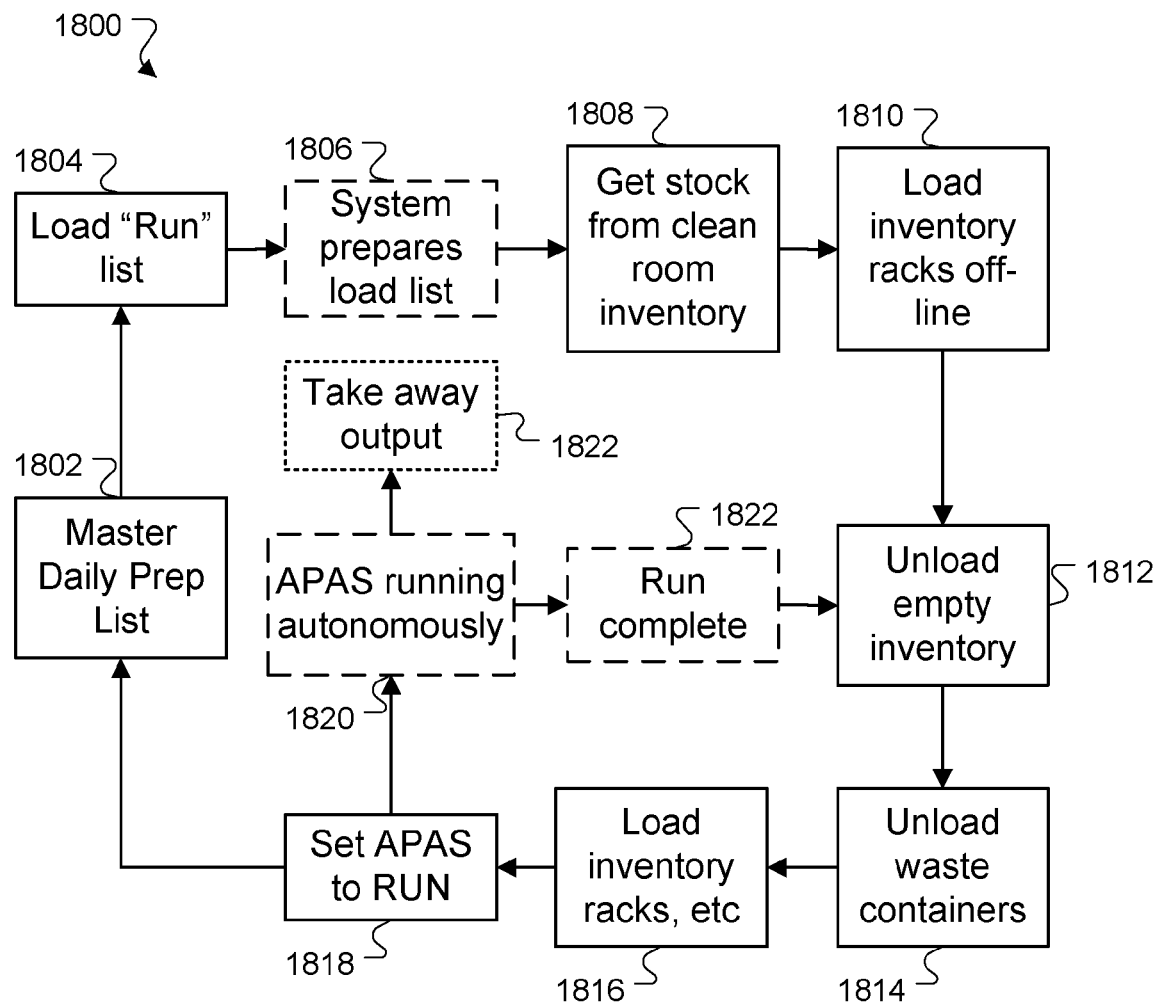
FIG. 18 is a flow chart of an example batch mode method that may be used by the exemplary device of FIG. 1.

FIG. 18 is a flow chart of a batch mode of operation that may be used to fill orders provided to the APAS. Batch mode 1800 involves the loading of the APAS with a batch of input drugs and diluents and syringes and IV bags for the output doses to produce a pre-defined set of drug orders. An operator, for example, prepares a master daily prep list 1802, which is a list of all the drug orders that need to be filled by the APAS for that day. This may include, for example, many prescriptions of one type or a variety of different prescriptions. The list is next loaded, in whole or in part (e.g., depending on the size of the list), into the APAS as the "run" list 1804 to be used by the APAS to prepare the drug orders. Software in the APAS screens the drug orders to ensure that the APAS is trained to fill them. The APAS then identifies the inventory required to fill the drug orders and the rack configurations from those available. It prepares a load list 1806 to guide the loading of the inventory into the racks. The inventory needed includes the drugs and diluents needed to prepare the orders, which may be contained, for example, in vials, syringes, or IV bags. It also includes the syringes (with needles fitted) required for processing the orders and the output containers for the drug doses, which may include a syringe or an IV bag, for example. From this load list, an operator gets stock from clean room inventory 1808, for example, and loads the inventory racks offline 1810 with the stock in the positions on the racks as indicated by the load list.

Next the operator delivers the racks to the APAS. The operator then follows an inventory loading process as described in FIG. 4, first unloading empty inventory 1812 or unused inventory that may be contained on the carousels from the prior run. The operator then unloads waste containers 1814 and empties them in preparation for the run. The waste containers are below the waste chutes 333, described in FIG. 3, and may hold empty containers (e.g., used or empty syringes, bags, vials) that were used by the APAS. Next, in the inventory loading process as described in FIG. 4, the operator loads the inventory racks 1816 onto the carousels. The operator begins the batch process by setting the APAS to RUN 1818, for example, by selecting the RUN button on a touch screen flat panel monitor, an example of which is the monitor 202. The APAS then runs autonomously 1820, generating the output orders which, depending on the drug container, will be dropped into the syringe discharge chute 332 or the IV bag discharge chute 344, described in FIG. 3, where a receptacle placed beneath each chute will gather the containers. A pharmacy staff member will take the output away 1822 to be placed in inventory, for example, in a hospital ward.

The APAS will continue to run and prepare the drug orders until its run is complete 1822. The operator will be informed of this by, for example, the displaying of a message on a flat panel monitor serving as the input/output device 306, as described in FIG. 3. The run will complete if the entire rack inventory has been depleted or the orders for the day have been completed.

Figure 19:
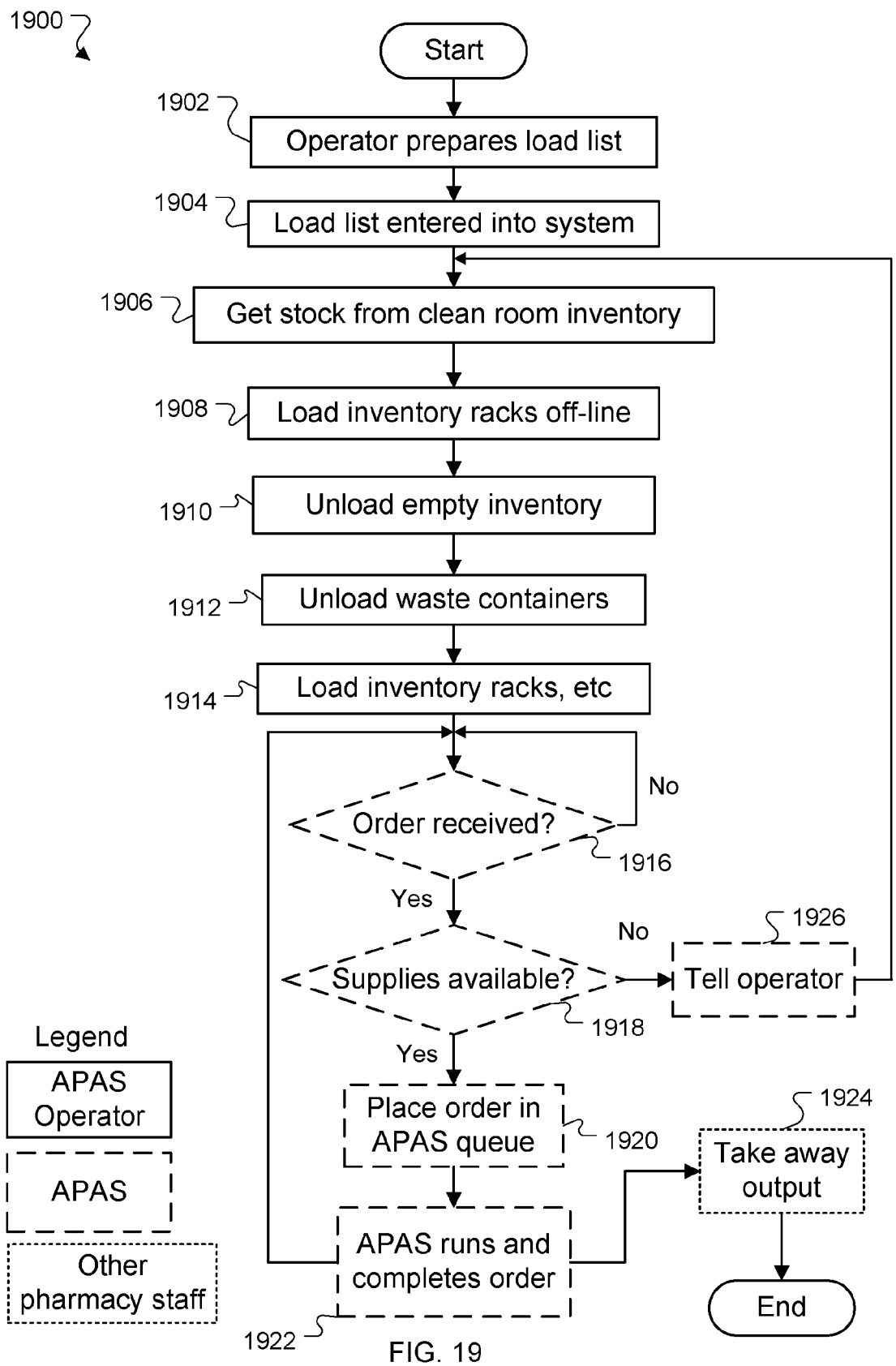
FIG. 19 is a flow chart of an example on-demand mode method that may be used by the exemplary device of FIG. 1.

FIG. 19 is a flow chart of an on-demand mode of operation that may be used to fill orders provided to the APAS. On-demand mode 1900 involves the loading of the APAS with a complement of input drugs and diluents and syringes and IV bags for the output doses to produce drug orders that would constitute the most common drugs used on a given day. An operator prepares a load list 1902 to guide the loading of the inventory into the racks. The inventory needed includes the complement of drugs and diluents needed, which may be contained, for example, in vials, syringes, or IV bags. It also includes the output container for the drug dose, which may be a syringe or an IV bag, for example. The operator enters the load list into the APAS 1904 using, for example, the flat panel monitor 202 as described in FIG. 2. From this load list, an operator gets stock from clean room inventory 1906, for example, and loads the inventory racks offline 1908 with the stock in the positions on the racks as indicated by the load list.

Next the operator delivers the racks to the APAS. The operator then follows an inventory loading process as described in FIG. 4, first unloading empty inventory 1910 or unused inventory that may be contained on the carousels from the prior day's operation. The operator then unloads waste containers 1912 and empties them in preparation for the day's orders. The waste containers are below the waste chutes 333, described in FIG. 3, and hold empty containers that were used by the APAS. Next, in the inventory loading process as described in FIG. 4, the operator loads the inventory racks 1914 onto the carousels.

The APAS then waits to receive drug orders 1916 from the hospital pharmacy by way of the hospital network, for example, as was described in FIG. 2. When an order is received by the hospital pharmacy, it is entered into the APAS. The APAS checks to make sure the necessary supplies 1918 are in place to fill the order. If they are, the order is placed into the queue for the APAS 1920 where the APAS will then run and complete the orders 1922. The output order, depending on the drug container, will be dropped into the syringe discharge chute 332 or the IV bag discharge chute 344, as described in FIG. 3, where a receptacle placed beneath each chute will hold the container. A pharmacy staff member will take the output away 1924 to be used that day, for example, in a hospital ward.

If, when an order is received, the APAS determines that the necessary supplies 1918 needed to fill the order are not in place, it notifies the operator 1926 who is responsible for reloading the inventory into the machine 1906.

The APAS will be able to run in either the batch mode or on-demand mode depending on user needs. For example, it can be used in the on-demand mode during the day shifts responding to demand from the hospital as it arises. During the evening and night shifts, it can be producing batches of drugs that are carried in bulk in the hospital pharmacy to maintain inventory.

An exemplary system 2000 capable of registering a fill port with stationary IV bags is shown in FIGS. 20A-20D. Embodiments may perform fluid transfer in needle-down or needle-up orientation. Registration may involve a portable fluid transfer port and/or a stationary bag, for example.

Figure 20A:
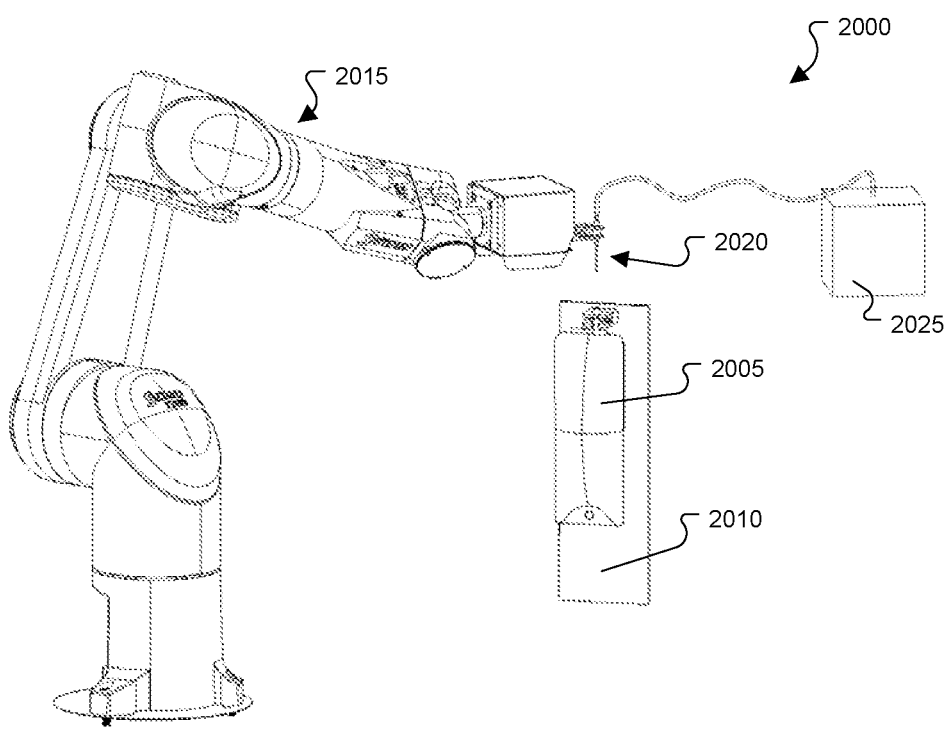
FIGS. 20A-20D show exemplary operations for a robotic manipulator to register a fill port with an IV bag in needle-up and needle-down orientations.

Embodiments may be operated by a controller to perform a process wherein an IV bag is conveyed from a carrier to a parking fixture in the cell and parked there by a robotic manipulator 2015. In the example of FIG. 20A, the system 2000 includes an exemplary parking fixture 2010, which may, in some embodiments, be the IV bag manipulator of FIG. 17A. In other embodiments, the parking fixture 2010 may also be a rack holding one or more IV bags that may be manually loaded by an operator.

The robot manipulator 2015, having released the IV bag 2005, may then grasp a fluid transfer port 2020 and register the port into the needle port on the IV bag. The fluid transfer port 2020 is connected to a fluid transfer device 2025, which can transfer fluid into and out of the IV bag (e.g., using gravity feed, pump, or other transfer mechanism). Air in the top of the bag could be drawn from it first with the means described elsewhere in this document if the bag is oriented so that the port is at the top of the bag. The bag could also be restrained on an IV bag manipulator and be inverted for drawing of fluid from the bag as shown in the Figure below.

Figure 20B:
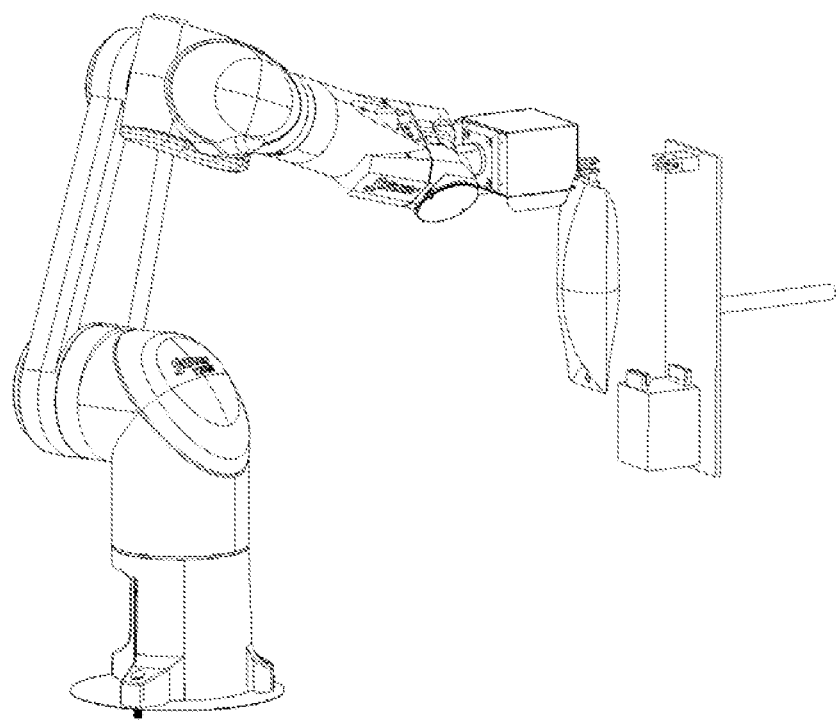
Figure 20C:
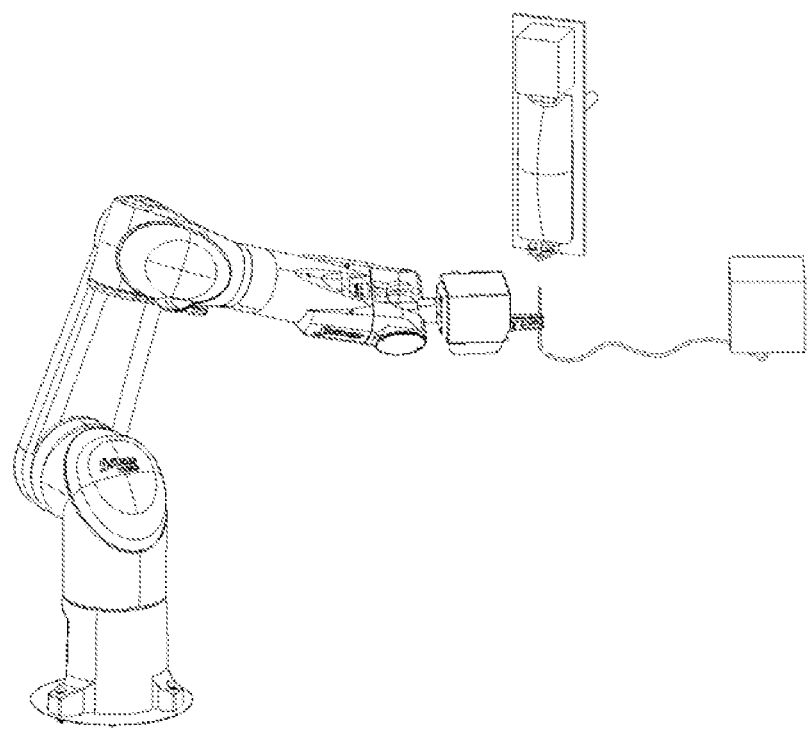
Figure 20D:
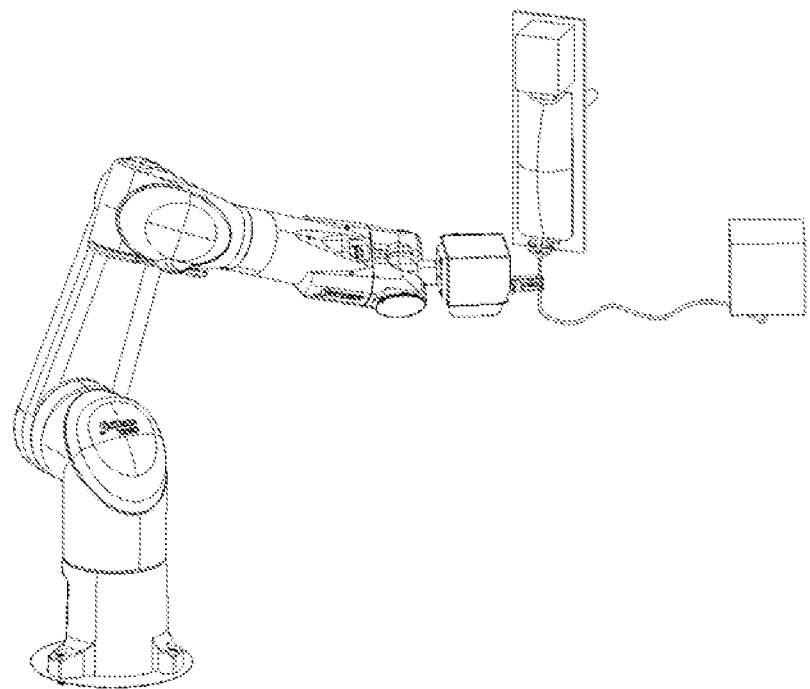

As illustrative embodiments, FIG. 20A shows the bag being parked and the robotic manipulator grasping and registering the fluid transfer port into the needle port on the bag. FIG. 20B shows the robotic manipulator placing the IV bag in IV Bag Manipulator. FIG. 20C shows the robotic manipulator grasping the fluid transfer port. FIG. 20D shows the robotic manipulator registering the fluid transfer port to the IV bag needle port.

In alternate embodiments, one or more IV bags may be mounted to retention clips, for example, such as may be mounted on a rotating storage carousel or a flat carrier. The robotic manipulator may register the fluid transfer port with any of the stationary bags. In a further alternate embodiment, the 2, 3, 4 or more IV bags may be retained by fill port retention clips coupled to an indexer, such as the indexer 1512 that was described with reference to FIG. 15.

In addition to the above-described examples, IV bags and syringes may be handled using systems, apparatus, methods, or computer program products other than the examples described above.

For example, the APAS 100 may include a main controller and one or more additional controllers in a distributed network architecture. The main controller may provide supervisory and management of cell operations, and coordinate the performance of sub-operations by the other controllers. Each controller may include one or more processors that perform operations according to software that may be developed, and compiled using one or more languages. The controllers may be in the form of embedded systems, having dedicated controllers, PLCs (programmable logic controllers), PC-based controllers with appropriate networking and I/O hardware and software, ASICs, or other implementation.

In some applications, one controller may be dedicated to controlling the robotic manipulator, including determining the position and motion paths for the manipulator within the processing chamber. Motion planning may involve solving the dynamic kinematic equations to optimize conveyance time and reduce energy consumption, and such computation may be accomplished in real-time with a math co-processor and/or digital signal processor that may be local to the APAS cell, or available on a remotely located workstation coupled to the APAS through a network connection, for example. In other embodiments, the expected motions (e.g., from carousel to scale) of the robot manipulator may be learned or taught.

Databases may be provided for purposes of handling various types and sizes of IV bags, syringes, and vials, as well as the expected locations and orientations for various inventory items on the storage carousels, racks, and the various stations throughout the processing chamber. Motion, position, force, diameter, and similar parameters may be compared against upper and lower thresholds in some cases, to determine if the manipulator has encountered a condition that should trigger and error signal, alarm, email notification, instant message, paging signal, or other signal to a responsible pharmacist, operator, or system maintainer, for example.

To accommodate various size, type, and manufacture of IV bags, appropriately sized holders may be disposed at locations in the cell at which the IV bag may be parked by the manipulator. Based upon information sufficient to associate an IV bag with a suitable holder, the information being determined either from user input or auto-detected (e.g., by bar code), the manipulator may selectively park the IV bag at the holder most compatible with the IV bag it is handling or conveying. With reference to FIG. 15A, for example, multiple styles and designs of the IV bag retention clips 1506 may be mounted to the indexer 1512 so that the manipulator may park an IV bag on a selected holder most appropriate for the IV bag. This approach may also be applied to storage racks and various stations disposed in the processing chamber.

In some embodiments, the indexer 1512 may move the waste vial 1516, the IV bag 1508, and the vial containing drug to be reconstituted (see FIGS. 15A-15C) laterally and or vertically to register the appropriate item in alignment with the needle 1514 of the syringe 1510. In alternate embodiments, the needle down syringe manipulator may move the syringe and needle vertically and/or horizontally relative to the waste vial 1516, the IV bag 1508, and the vial containing drug to be reconstituted.

In some embodiments, the robotic manipulator may directly register an item it is grasping and holding, such as an IV bag fill port or a syringe, to implement a fluid transfer operation. The fluid transfer or gas extraction processing may be performed with the robotic arm grasping and supporting at least one of the containers involved in the fluid transfer operation.

Some systems may be implemented as a computer system that can be used with implementations of the invention. For example, various implementations may be implemented in digital electronic circuitry, or in computer hardware, firmware, software, or in combinations of them. Apparatus can be implemented in a computer program product tangibly embodied in an information carrier, e.g., in a machine-readable storage device or in a propagated signal, for execution by a programmable processor; and methods can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

To provide for interaction with a user, the invention can be implemented on a computer having a display device such as a CRT (cathode ray tube) or LCD (liquid crystal display) monitor for displaying information to the user and a keyboard and a pointing device such as a mouse or a trackball by which the user can provide input to the computer.

The computer system may be implemented as a distributed computing system, and can include clients and servers. A client and server are generally remote from each other and typically interact through a network. The relationship of client and server arises by virtue of computer programs running on the respective computers and having a client-server relationship to each other.

The invention can be implemented in a computer system that includes a back-end component, such as a data server, or that includes a middleware component, such as an application server or an Internet server, or that includes a front-end component, such as a client computer having a graphical user interface or an Internet browser, or any combination of them. The components of the system can be connected by any form or medium of analog or digital data communication, including packet-based messages, on a communication network. Examples of communication networks include, e.g., a LAN, a WAN, wireless and/or optical networks, and the computers and networks forming the Internet.

In various embodiments, systems such as those described herein for handling IV bags and/or syringes, among other items, may communicate information using suitable communication methods, equipment, and techniques. For example, the APAS controller may communicate with the hospital LAN and/or a hospital pharmacy network using point-to-point communication in which a message is transported directly from the source to the receiver over a dedicated physical link (e.g., fiber optic link, point-to-point wiring, daisy-chain). Other embodiments may transport messages by broadcasting to all or substantially all devices that are coupled together by a communication network, for example, by using omni-directional radio frequency (RF) signals, while still other embodiments may transport messages characterized by high directivity, such as RF signals transmitted using directional (i.e., narrow beam) antennas or infrared signals that may optionally be used with focusing optics. Still other embodiments are possible using appropriate interfaces and protocols such as, by way of example and not intended to be limiting, RS-232, RS-422, RS-485, 802.11 a/b/g, Wi-Fi, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

In some embodiments, each APAS system may be programmed with the information and be initialized with substantially identical information stored in non-volatile memory. In other embodiments, one or more APAS systems may be custom configured to perform specific functions. For example, one APAS system may be configured to perform both custom and batch processing functions by responding to information about the compounding needed to fulfill various prescriptions and information about various alternative inventory solutions.

In various embodiments, the APAS 100 may work with inventory items, such as IV bags, vials, and syringes from various manufacturers. In some implementations, IV bag fill port retention clips placed at various proximate various stations in the processing chamber, and/or the gripper fingers on the robotic arm, may be exchanged or interchanged as needed to accommodate various designs and types of inventory items. Advantageously, some embodiments of the gripper fingers, for example, can accommodate a wide range of sizes and designs of commercially available inventory items, as described above.

In an embodiment, compounding operations may be performed using commercially available containers adapted for parenteral applications. APAS can also accommodate parenteral fluid containers, for example, those used for the preparation of total parenteral nutrition. In one example, such containers may be processed as inputs and/or outputs from the APAS 100. In further embodiments, compounding operations may be performed using commercially available flexible fluid containers for certain other medical or pharmaceutical applications. As an example, such containers may be processed as inputs and/or outputs from the APAS 100.

In some applications, compounding operations may be performed according to aspects of embodiments described herein in a clean environment. For example, an embodiment may be performed in a clean room environment, such as an ISO Class 5 environment, for example. In another embodiment, compounding operations may be implemented in a ventilated (e.g., flow hood) work area. In other embodiments, compounding operations may be performed in a chamber, an example of which is the compounding chamber 304. In various implementations, a series of compounding processes may be performed in part within a chamber, flow hood, and/or clean room. In various embodiments, the compounding operations, the inventory storage, and/or the actuation and conveyance of items may be performed in a substantially aseptic environment. In various embodiments, the compounding chamber 304 may be at a negative pressure relative to ambient atmospheric pressure, and the inventory chamber 302 may be at a positive pressure relative to ambient atmospheric pressure.

In conjunction with the compounding area, inventory items may coordinate the handling of inventory items with a carrier that may present one or more items within proximity of a manipulator, for example. In an embodiment, one or more inventory items may be presented or delivered to a manipulator, an example of which is the robotic arm 318.

The manipulator system may include one or more coordinated axes of motion to grasp, convey, and/or orient inventory items. An inventory item may be, for example, registered on a retainer clip on a storage rack, or registered with a fluid transfer port, or otherwise manipulated in support of operations, such as operations involving fluid transfers at a fluid transfer station, that relate to compounding. In embodiments, the manipulator system may convey items in part by gravity feed system, or motion imparted by one or more motors (e.g., electric motors), operating alone or in combination.

In some embodiments, inventory delivered to the robotic arm 318 in the APAS 100, for example, may be a syringe that includes a syringe barrel in combination with a needle operably coupled to the barrel. In some embodiments, the needle is capped, and the needle cap is removed as a preparatory step for operating the syringe in various compound processing steps.

In some embodiments, the pressure in a chamber of the APAS may be different from ambient, such as up to at least about 10 inches of water, or between about 0.1 and 1.0 inches of water above or below ambient atmospheric pressure. Negative pressure may reduce the likelihood that certain chemicals may be released outside the chamber, for example.

A number of implementations of the invention have been described. Nevertheless, it will be understood that various modifications may be made without departing from the spirit and scope of the invention. For example, advantageous results may be achieved if the steps of the disclosed techniques were performed in a different sequence, if components in the disclosed systems were combined in a different manner, or if the components were replaced or supplemented by other components. The functions and processes (including algorithms) may be performed in hardware, software, or a combination thereof, and some implementations may be performed on modules or hardware not identical to those described. Accordingly, other implementations are within the scope that may be claimed.

What is claimed is:

1. An automated pharmacy admixture system, comprising:
a carrier system to present a plurality of IV bags to a location proximate or within a first substantially aseptic zone, wherein the carrier system is substantially disposed in a second substantially aseptic zone, wherein a pressure within the first aseptic zone is negative relative to ambient atmospheric pressure;
a manipulator system to transport items within the first substantially aseptic zone;
a fluid transfer system disposed at least substantially within the first substantially aseptic zone, the fluid transfer system comprising a fluid transfer port to transfer fluids to or from IV bags; and
a controller comprising a processor to receive instructions that, when executed by the processor, cause the processor to perform operations comprising:
actuating the manipulator system to bring a fill port of an IV bag and the fluid transfer port into register with one another, and
actuating the manipulator system to move the IV bag and the fluid transfer port out of register after a fluid transfer operation.

2. An automated pharmacy admixture system comprising:
a supply of IV bags, each bag having at least one of a plurality of different fill port configurations;
a substantially aseptic chamber comprising at least one fluid transfer station configured to transfer fluids into or out of an IV bag, wherein a pressure inside the substantially aseptic chamber is negative relative to ambient atmospheric pressure;
a carrier that delivers the supply of IV bags to a location proximate the substantially aseptic chamber; and
an actuator to convey the IV bags to one or more of the fluid transfer stations within the chamber.

3. An automated pharmacy admixture system, comprising:
a carrier system comprising a rotating carousel to present a plurality of different types of medical containers to a location proximate or within a first substantially aseptic zone that is controlled to maintain a pressure level negative relative to ambient atmospheric pressure, wherein the plurality of different types of medical containers comprise items selected from the group consisting of syringes, IV bags, and vials, and wherein the carrier system is substantially disposed in a second substantially aseptic zone;
a robotic manipulator system to handle the plurality of different types of medical containers within the first substantially aseptic zone;
a fluid transfer system disposed at least substantially within the first substantially aseptic zone, the fluid transfer system comprising a fluid transfer port to transfer fluids to or from the medical containers; and
a controller comprising a processor to receive instructions that, when executed by the processor, cause the processor to perform operations comprising:
actuating the robotic manipulator system to transfer an IV bag or vial to the fluid transfer system;
bringing a fill port of the IV bag or vial and the fluid transfer port into register with one another;
moving the fill port and the fluid transfer port out of register after a fluid transfer operation; and
actuating the robotic manipulator system to remove the IV bag or vial from the fluid transfer system.

4. The system of claim 3, wherein the rotating carousel comprises at least one device to releasably retain a fill port of an IV bag.

5. The system of claim 4, wherein the retaining device comprises a clip.

6. The system of claim 3, wherein the rotating carousel is configured to hold different sizes or shapes of syringes, IV bags, and vials.

7. The system of claim 3, wherein a pressure in the first substantially aseptic zone is regulated to a pressure level substantially below ambient pressure.

8. The system of claim 7, wherein the pressure level in the first substantially aseptic zone is between about 0.1 and about 10 inches of water below ambient pressure.

9. The system of claim 3, wherein the second substantially aseptic zone is regulated to a pressure level substantially above or below ambient pressure.

10. The system of claim 9, wherein the pressure level in the second substantially aseptic zone is higher than the first substantially aseptic zone.

11. The system of claim 3 further comprising a UV (ultraviolet) sanitization system to sanitize at least a portion of the fill port of the IV bag or vial.

12. The system of claim 3, wherein the fluid transfer system is configured to inject a predetermined amount of air into a vial to facilitate the withdrawal of fluid from the vial.

13. The system of claim 3, wherein the fluid transfer port comprises a port of a needle on a syringe and is coupled to exchange fluid with a medical container while the needle is oriented substantially upward.

14. The system of claim 3, wherein the fluid transfer port comprises a port of a needle on a syringe and is coupled to exchange fluid with a medical container while the needle is oriented substantially downward.

15. The system of claim 3 further comprising an ID station to identify medical containers so as to confirm that a medical container being handled by the robotic manipulator system is the appropriate medical container for a selected operation.

16. The system of claim 3 further comprising a weighing station to weigh medical containers to confirm that that a predetermined amount of fluid has been transferred to or from the containers.

17. The system of claim 3 further comprising a needle decapping station to automatically remove needle caps in preparation for a compounding operation.

18. The system of claim 3 further comprising a needle removing station to automatically remove a needle from a syringe after the syringe has been loaded with a desired quantity of medication.

19. The system of claim 18 further comprising a syringe capping station to place a cap on the syringe after the needle has been removed.

20. The system of claim 3 further comprising a manual loading station where an operator loads medical containers onto the carrier system.

21. An automated pharmacy admixture system, comprising:
a processing chamber that provides a substantially aseptic environment for a preparation of one or more pharmaceutical doses, wherein the system is configured to maintain a pressure level inside the processing chamber that is substantially below an atmospheric pressure level proximate and exterior to the processing chamber to substantially reduce an egress of chemicals from inside the processing chamber to outside the processing chamber;

an inventory chamber exterior and adjacent to the processing chamber for storing within an interior of the inventory chamber a plurality of inventory items to be used in the preparation of one or more pharmaceutical doses, wherein the plurality of inventory items comprises at least one container of diluent, at least one medication container including medication, and at least one syringe, each of the at least one syringes comprising a plunger disposed within a first end of a barrel and a needle coupled to a second opposite end of the barrel, wherein the inventory chamber substantially encloses the plurality of inventory items in an environment substantially separate from an ambient environment outside of the inventory chamber;

a rotatable inventory carousel disposed in the inventory chamber and rotatable around a vertical axis, the inventory carousel operable to support the plurality of inventory items;

an exterior access portal in a side of the inventory chamber, wherein the exterior access portal is operable from a closed position to an open position to provide an operator access to the plurality of inventory items stored within the inventory chamber;

a multiple degree of freedom robotic arm disposed within the processing chamber and configured to reach into the inventory chamber, retrieve an inventory item being supported by the inventory carousel, present the inventory item to a first process location in the processing chamber, release the inventory item for processing at the first process location, and subsequently retrieve the inventory item and convey the inventory item to a second process location;

an opening defined in a side between the inventory chamber and the processing chamber wherein the opening is arranged to permit the robotic arm to reach through the opening and grasp a selected inventory item supported by the inventory carousel within the inventory chamber;

a syringe manipulator station within the processing chamber that is configured to hold the syringe;

a waste container situated to receive processed inventory items from the robotic arm; and a controller that is configured to cause steps to be performed to prepare a pharmaceutical dose in an output container, the steps comprising:

(a) selecting at least one of each of the at least one syringe, the at least one diluent container, and the at least one medication container to be used to prepare an output container that comprises a pharmaceutical dose;

(b) rotating the inventory carousel to at least one position to make at least one of the selected syringe, the selected diluent container, and the selected medication container accessible by the robotic arm as the robotic arm reaches through the opening;

(c) conveying the selected syringe and the selected diluent container to the syringe manipulator station using the robotic arm;

(d) registering the needle of the selected syringe with a port of the selected diluent container and drawing diluent from the selected diluent container into the selected syringe;

(e) conveying the selected medication container to the syringe manipulator station using the robotic arm; and (f) registering the needle of the selected syringe with a port of the selected medication container to inject at least a portion of the diluent that was drawn into the syringe in order to reconstitute the medication in the selected medication container.

22. The automated pharmacy admixture system of claim 21, wherein the steps further comprise rotating the inventory carousel to make each of the selected syringe, the selected diluent container, and the selected medication container accessible by the robotic arm as the robotic arm reaches through the opening.

23. The automated pharmacy admixture system of claim 21, wherein the waste container is disposed in a chamber disposed beneath the processing chamber.

24. The automated pharmacy admixture system of claim 21, wherein the container of diluent comprises an IV bag.

25. The automated pharmacy admixture system of claim 24, further comprising an IV bag holding station adapted to receive the IV bag from the robotic arm and operable to rotate between a first position configured to support the received IV bag with a port of the IV bag directed substantially upwards, and a second position configured to support the received IV bag with the port of the IV bag directed substantially downwards, wherein the IV bag holding station is further adapted to register the port of the IV bag with the needle of the syringe held by the syringe manipulator station while the IV bag station is in either the first position or the second position.

26. The automated pharmacy admixture system of claim 25, wherein the robotic arm is adapted to convey the IV bag to an egress area after the IV bag has been processed to include a reconstituted medication.

27. The automated pharmacy admixture system of claim 21, wherein the robotic arm is adapted to convey the syringe to an egress area after the syringe has been processed to include a reconstituted medication.

28. The automated pharmacy admixture system of claim 21, wherein the medication container comprises a vial.

29. The automated pharmacy admixture system of claim 21, wherein the inventory chamber comprises an inventory monitoring system that includes a barcode scanner arranged to monitor position information about at least one of the plurality of inventory items supported by the inventory carousel by scanning one or more barcodes coupled to the inventory carousel and associated with at least one of the inventory items supported by the inventory carousel.

30. The automated pharmacy admixture system of claim 21, wherein the syringe stored within the interior of the inventory chamber further comprises a needle cap covering the needle.

31. The automated pharmacy admixture system of claim 30, further comprising a needle decapper station at which the system operates to separate the needle cap from the syringe.

32. The automated pharmacy admixture system of claim 21, wherein the first process location or the second process location comprises a weight scale for measuring a weight of the retrieved inventory item.

33. The automated pharmacy admixture system of claim 21, wherein the first process location or the second process location comprises the syringe manipulator station.

34. The automated pharmacy admixture system of claim 21, wherein the steps further comprise rotating the inventory carousel to make at least two of the selected syringe, the selected diluent container, and the selected medication container accessible by the robotic arm as the robotic arm reaches through the opening.

* * * * *

UNITED STATES PATENT AND TRADEMARK OFFICE
CERTIFICATE OF CORRECTION

| | | |
|---|---|---|
| PATENT NO. | : 7,610,115 B2 | Page 1 of 1 |
| APPLICATION NO. | : 11/316795 | |
| DATED | : October 27, 2009 | |
| INVENTOR(S) | : Ronald H. Rob et al. | |

It is certified that error appears in the above-identified patent and that said Letters Patent is hereby corrected as shown below:

Column 1, line 9, please delete "And" and insert --and-- therefor;

Column 1, line 10, before "contents" please insert --entire--;

Column 26, line 46 (Claim 16), after "confirm that" please delete "that".

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,610,115 B2 |
| APPLICATION NO. | : 11/316795 |
| DATED | : October 27, 2009 |
| INVENTOR(S) | : Rob et al. |

Page 1 of 1

It is certified that error appears in the above-identified patent and that said Letters Patent is hereby corrected as shown below:

On the Title page,

[*] Notice: Subject to any disclaimer, the term of this patent is extended or adjusted under 35 USC 154(b) by 633 days Delete the phrase "by 633 days" and insert -- by 859 days --

Signed and Sealed this

Twenty-second Day of June, 2010

David J. Kappos
*Director of the United States Patent and Trademark Office*